United States Patent
McBride et al.

(10) Patent No.: US 10,939,712 B1
(45) Date of Patent: Mar. 9, 2021

(54) HELMETLESS SUPPORT AND VENTILATION SYSTEM FOR A SURGICAL HOOD AND GOWN AND METHODS OF MAKING AND USING SAME

(71) Applicants: Mark McBride, Coronado, CA (US);
Philip H Salvatori, Salem, OR (US);
John Roughneen, Coronado, CA (US);
Carola Romero, San Diego, CA (US);
Nathan Satter, West Linn, OR (US)

(72) Inventors: Mark McBride, Coronado, CA (US);
Philip H Salvatori, Salem, OR (US);
John Roughneen, Coronado, CA (US);
Carola Romero, San Diego, CA (US);
Nathan Satter, West Linn, OR (US)

(*) Notice: Subject to any disclaimer, the term of this patent is extended or adjusted under 35 U.S.C. 154(b) by 0 days.

(21) Appl. No.: 16/894,938

(22) Filed: Jun. 8, 2020

(51) Int. Cl.
*A41D 13/11* (2006.01)
*A41D 13/002* (2006.01)
*A61G 10/00* (2006.01)
*A61H 33/14* (2006.01)
(Continued)

(52) U.S. Cl.
CPC ...... *A41D 13/1153* (2013.01); *A41D 13/0025* (2013.01); *A61G 10/00* (2013.01); *A61H 33/14* (2013.01); *A61M 21/0094* (2013.01); *A62B 31/00* (2013.01)

(58) Field of Classification Search
CPC ............ A41D 13/1153; A41D 13/0025; A41D 13/11; A41D 13/12; A41D 13/1209; A41D 13/1218; A41D 13/002; A41D 13/00; A42B 3/28; A42B 3/281; A42B 3/283; A42B 3/285; A42B 3/286; A42B 3/288; A42B 3/225; A42B 3/22; A42B 3/14; A42B 3/142; A42B 3/145; A42B 1/00; A42B 1/04; A42B 1/008; A62B 18/00; A62B 18/04; A62B 18/045; A62B 18/08; A62B 18/084; A62B 18/003; A62B 18/006; A62B 18/02; A62B 18/025; A62B 31/00; A62B 17/00; A62B 17/04; A62B 17/005;
(Continued)

(56) References Cited

U.S. PATENT DOCUMENTS 6,367,085 B1 * 4/2002 Berg ..................... A42B 3/145
128/201.24
2015/0297920 A1 * 10/2015 Takeuchi ........... A41D 13/0025
2/455

FOREIGN PATENT DOCUMENTS

CA 2825277 8/2012

* cited by examiner

*Primary Examiner* — Clinton T Ostrup
*Assistant Examiner* — F Griffin Hall
(74) *Attorney, Agent, or Firm* — James R. McDaniel

(57) ABSTRACT

A helmetless support and ventilation system for use with surgical hoods and gowns, including a flexible band, a plurality of front offsets connected to the flexible band, an offset extension such that the plurality of front offsets is connected to the offset extension and the offset extension is located away from the flexible band, a plurality of faceplate attachment extensions, wherein each of the plurality of faceplate attachment extensions is connected to the offset extension, a plurality of support faceplate attachments, such that each of the plurality of support faceplate attachments are connected to each of the plurality of faceplate attachment extensions, and a ventilation system located within a surgical gown and a surgical hood for providing filtered, ventilation air within the surgical gown and the surgical hood, wherein the ventilation system is retained by shoulders of a wearer of the ventilation.

8 Claims, 21 Drawing Sheets

(51) Int. Cl.
*A62B 31/00* (2006.01)
*A61M 21/00* (2006.01)

(58) Field of Classification Search
CPC ........... A61F 9/06; A61F 9/068; A61G 10/00; A61H 33/14; A61M 21/0094
USPC ........ 2/410, 171.3, 457; 128/200.28, 201.22, 128/201.23, 201.24, 201.29, 202.19, 857; 600/21
See application file for complete search history.

HELMETLESS SUPPORT AND VENTILATION SYSTEM FOR A SURGICAL HOOD AND GOWN AND METHODS OF MAKING AND USING SAME

FIELD OF THE INVENTION

The present invention is generally related to support and ventilation systems for use with surgical hoods and gowns. The support and ventilation system for use with surgical hoods and gowns of the present invention utilizes a helmetless support and lightweight ventilation system used in conjunction with the helmetless support. The gown or toga portion is a one-piece garment designed to sterilely cover the wearer when attached to the hood. The ventilation system will be incorporated into a lightweight and soft "yoke" that will drape over the wearer's shoulders such that only a HEPA filter of the ventilation system extends outside of the gown or toga. There will be control switches on the ventilation system to allow the wearer to adjust the fan speed and, possibly, make other inputs.

BACKGROUND OF THE INVENTION

Prior to the present invention, as set forth in general terms above and more specifically below, it is known, to employ various types of support systems that are used to support the one-piece gown or toga which is designed to completely and sterilely cover the wearer when attached to the hood. Currently, a helmet is donned by the wearer and the one-piece gown or toga and the hood are conventionally attached to the helmet. Furthermore, it is known to provide a ventilation system that is also attached to the helmet or attached to the wearer.

Due to the fact that the weight of the helmet, the one-piece gown or toga, the hood, and the ventilation system are carried by the head, neck and shoulder areas of the wearer, after a period of time, the head, neck and shoulder areas of the wearer may begin to experience an undesirable amount of muscular fatigue or strain. Typically, the helmet, the one-piece gown or toga, the hood, and the ventilation system weigh around 3-5 pounds. Furthermore, it is common for a surgical procedure to last for several hours. Clearly, if the wearer of the one-piece gown or toga, the hood, and the ventilation system is bent over for several hours while performing the surgical procedure, the extra weight of the helmet, the one-piece gown or toga, the hood and the ventilation system can place a significant muscular strain on the head, neck, and shoulder areas of the wearer. Furthermore, having the weight on the top of the head makes for a longer lever arm to support the helmet when the head is tilted to any angle other than neutral which can also put undue stress on the head, neck, and shoulder areas of the wearer. While these and other various support systems that are used to support the one-piece gown or toga, hood and ventilation system may have been generally satisfactory, there is nevertheless a need for a new and improved helmetless support and lightweight ventilation system for use with surgical hoods and gowns.

It is a purpose of this invention to fulfill these and other needs in the art of support systems that are used to support the one-piece gown or toga, hood, and ventilation system in a manner more apparent to the skilled artisan once given the following disclosure.

The preferred helmetless support and lightweight ventilation system for use with surgical hoods and gowns, according to various embodiments of the present invention, offers the following advantages: ease of use; lightness in weight; durability; the ability to distribute the device weight along the shoulders of the wearer while maintaining full mobility and greatly reducing head and neck fatigue; adjustability of the fan speed; the ability to control the amount and direction of the output from each of the various ventilation system output apertures; the ability to provide a contiguous head/hood covering; the ability to filter the air contacting the wearer; the use of front offsets to provide for air circulation around the head and neck areas of the wearer; the ability to remove the face vents for ease of cleaning or sanitizing; the ability to provide air flow within the hood; and compactness of the device. In fact, in many of the preferred embodiments, these advantages are optimized to an extent that is considerably higher than heretofore achieved in prior, known support and ventilation systems for use with surgical hoods and gowns.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters, represent like parts throughout the several views and in which:

FIG. 8 is a schematic, rear view of the ventilation system for use with surgical hoods and gowns constructed according to an embodiment of the present invention;

DETAILED DESCRIPTION OF THE PREFERRED EMBODIMENTS OF THE INVENTION

Figure 1:
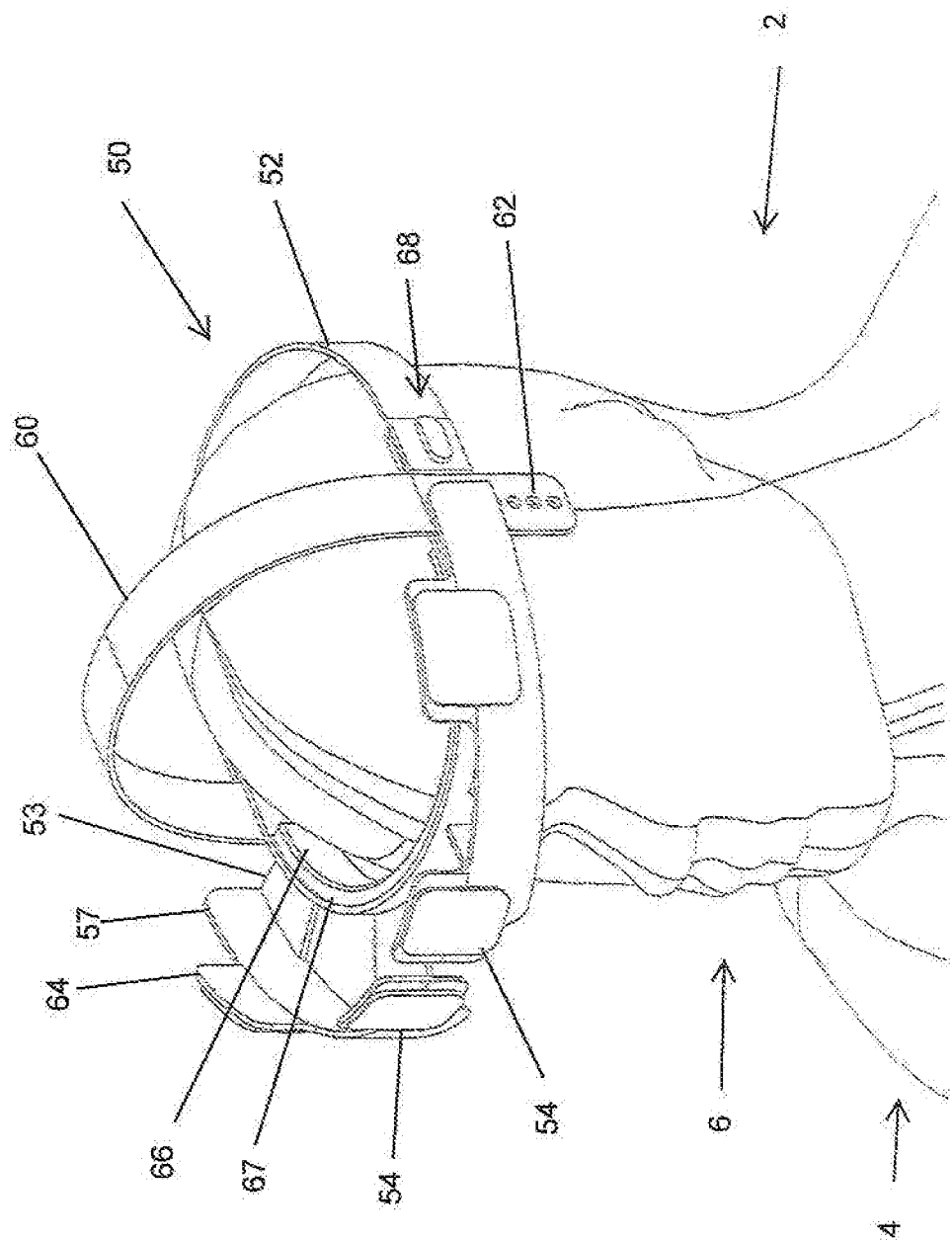
FIG. 1 is a schematic, top, isometric view of a helmetless support for use with surgical hoods and gowns, according to one embodiment of the present invention.
Figure 2:
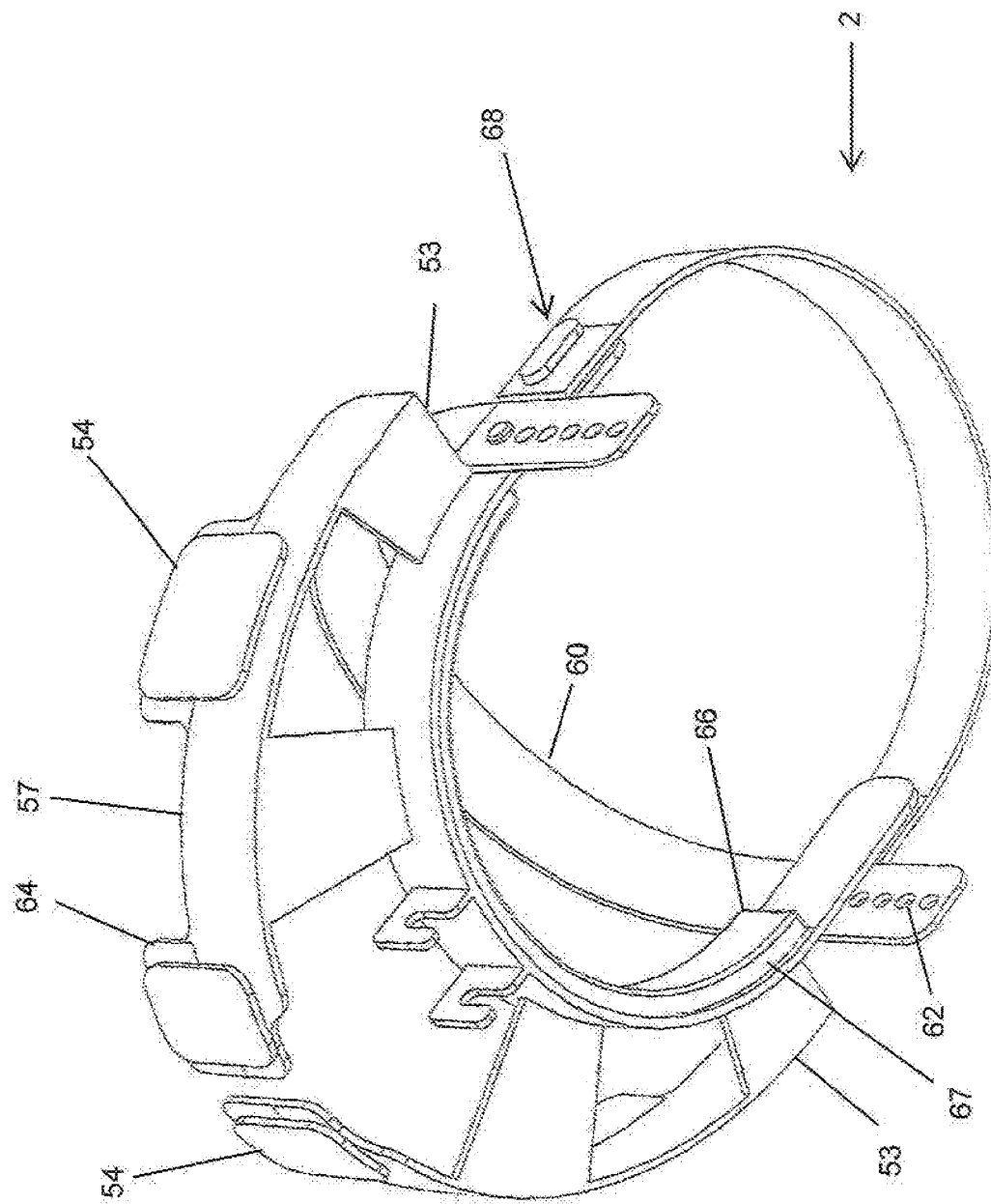
FIG. 2 is a schematic, bottom, isometric view of the helmetless support for use with surgical hoods and gowns prior to the faceplate being attached to the helmetless support, according to one embodiment of the present invention.
Figure 3:
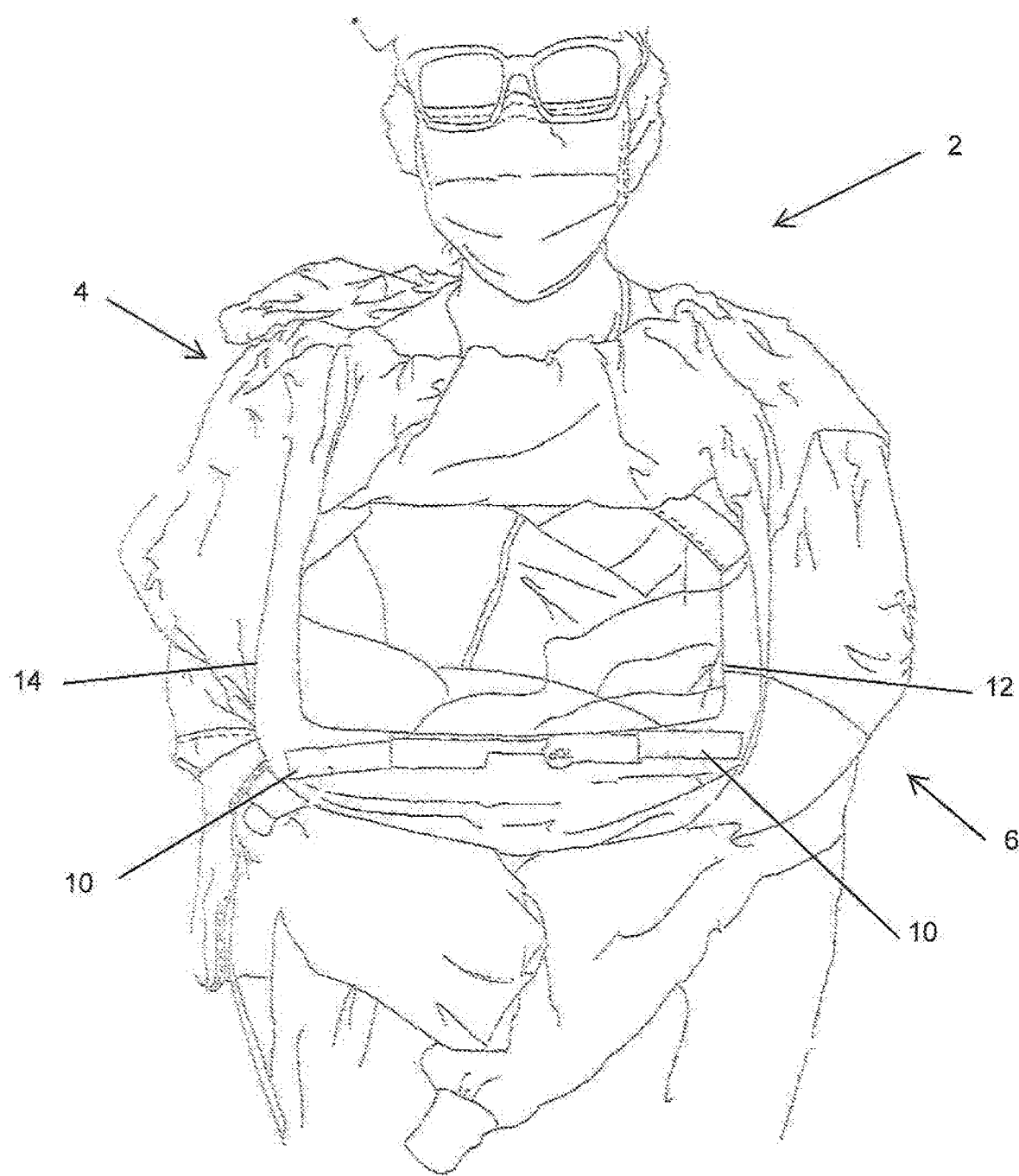
FIG. 3 is a schematic, front view of the surgical hood and gown prior to the faceplate being attached to the helmetless support, according to one embodiment of the present invention.

Referring now to FIGS. 1-5, there is illustrated a helmetless support system 2 for use with surgical hoods and gowns. The helmetless support system 2 for use with surgical hoods and gowns can be used to support the one-piece surgical gown 4 and the surgical hood 14 without the need for the wearer 6 to wear a helmet. In this manner, one-piece surgical gown 4 and the surgical hood 14 completely and sterilely covers the head, neck, and torso of the wearer 6 when donned by the wearer 6. Also, the one-piece surgical gown 4 and the surgical hood 14 includes a clear faceplate 12 (FIG. 3). The helmetless support 2 further includes a flexible headband 52 with attached lightweight front offsets 53 in front that can be releasably attached to the faceplate 12. Furthermore the front offsets 53 (FIG. 5) are used to provide for air circulation around head of the wearer 6.

Helmetless Surgical Hood and Gown Support

Figure 4:
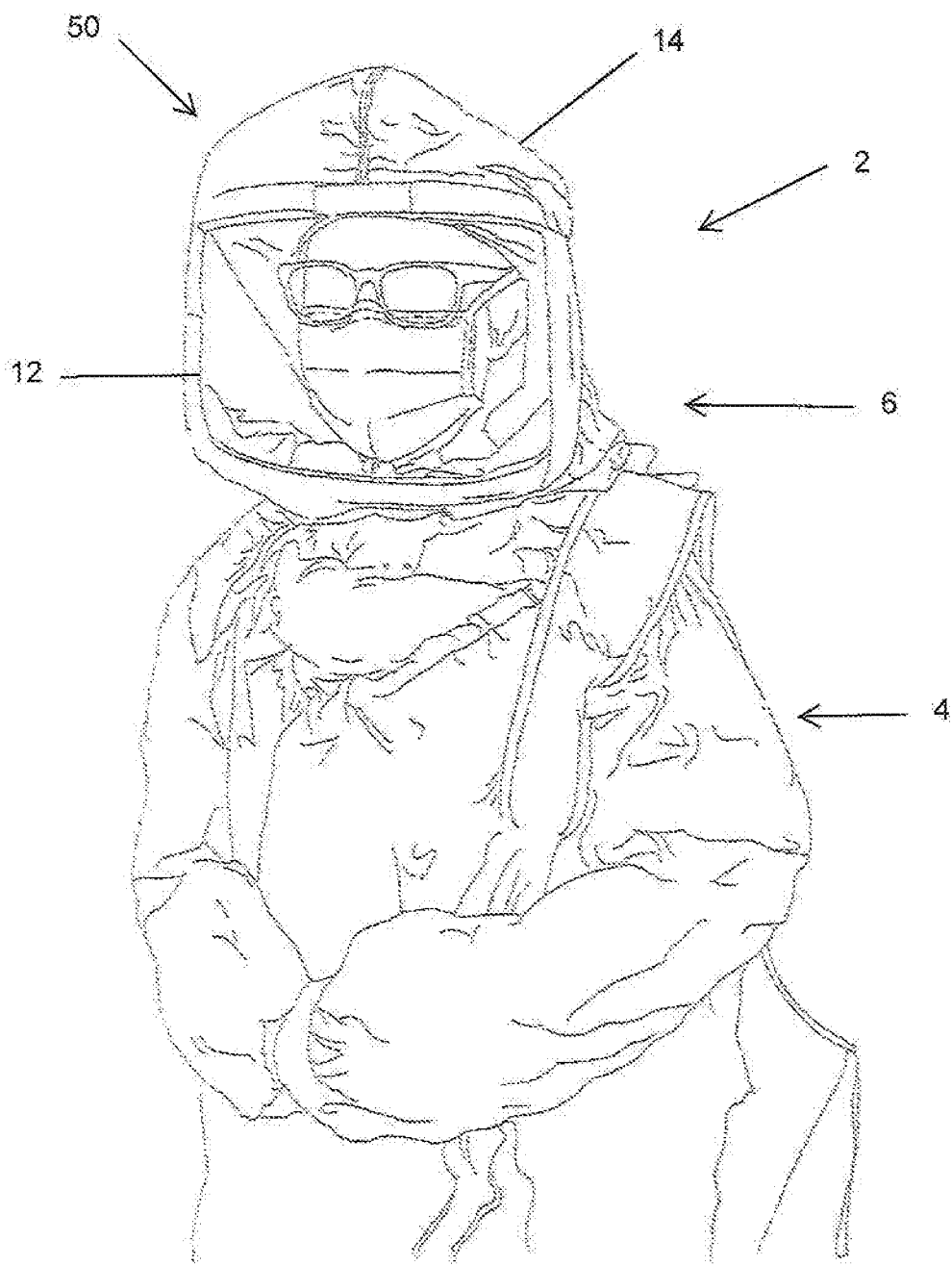
FIG. 4 is a schematic, isometric view of the helmetless support for use with surgical hoods and gowns with the faceplate being attached to the helmetless support, according to one embodiment of the present invention.

As shown in FIGS. 1 and 2, helmetless support 2 for use with surgical hoods and gowns includes, in part, surgical gown 4, wearer 6, and helmetless surgical hood and gown support 50. It is to be understood that surgical gown 4 is constructed of any suitable, durable, medical grade material. It is to be further understood that the surgical gown 4 is to be constructed into a one-piece design that will completely and sterilely cover the wearer when attached to the hood 14 (FIG. 4).

With respect to helmetless surgical hood and gown support 50, helmetless surgical hood and gown support 50 includes, in part, flexible, adjustable band 52, front offsets 53, faceplate attachments 54, offset extension 57, adjustable headband 60, adjustment openings 62, faceplate attachment extensions 64, sweat band 66, band pad 67, and band adjustment device 68. Preferably, flexible band 52 is constructed of any suitable, durable, flexible, medical grade material. The important feature of flexible band 52 being that it comfortably fits around the head of the wearer 6 but still is capable of securely holding surgical gown 4 and surgical hood 14 once the surgical gown 4 and surgical hood 14 have been attached to helmetless surgical hood and gown support 50 and then placed over the wearer, as will be discussed in greater detail later. In particular, it is important that flexible band 52 be able to securely hold hood 14 off of the head of wearer 6 and allow the air to flow around the head of wearer 6, as will be discussed in greater detail later.

A unique; aspect of the present invention is the use of front offsets 53, offset extensions 57, and faceplate attachment extensions 64. Preferably, there are at least two (2) front offsets 53 located along a perimeter on the front of flexible band 52 that hold the faceplate 12 of surgical hood 14 away from the face of wearer 6. Preferably, the front offsets 53 should extend be at least 1-3 inches outwardly away from flexible band 52 so that the front offsets 53 allow air to be circulated around the head of the wearer 6, as will be discussed in greater detail later. Preferably, front offsets 53, offset extensions 57, and faceplate attachment extensions 64 should be constructed of any suitable, durable, lightweight, medical grade material such as plastic or the like.

Another unique aspect of the present invention is faceplate attachments 54. Faceplate attachments 54 can be conventionally attached to offset extension 57 and faceplate attachment extensions 64 by conventional fasteners, adhesives, or the like. Preferably, faceplate attachments 54 are constructed of hook and loop fasteners (Velcro®) or magnets that will allow faceplate 12 to be easily attached to and removed from front offsets 53, as will be discussed in greater later.

With respect to FIGS. 1 and 2, another unique aspect of the present invention is the adjustable headband 60, adjustment openings 62, sweat band 66, band pad 67, and band adjustment device 68. In particular, the height of the adjustable headband above the head of the wearer 6 can be adjusted. In this manner, the wearer 6 can adjust the height that hood 14 is located above the head of the wearer 6 in order to adjust the flow of air around the upper part of the wearer's head. For example, the length of the adjustable headband 60 can be adjusted by selecting a desired adjustment opening 62 and conventionally locating the desired adjustment opening 62 on the adjustable headband 62. Furthermore, the circumference of the flexible band 52 can be adjusted by determining the desired flexible band 52 circumference for a particular wearer 6 and utilizing the band adjustment device 68 in order to retain the desired circumference of the flexible band 52.

A further unique aspect of the present invention is the use of sweat band 66 and band pad 67. In particular, when the wearer 6 dons the helmetless support system 2 for use with surgical hoods and gowns, the sweat band 66 contacts the forehead of the wearer 6 in order to substantially prevent any sweat from the forehead of the wearer 6 from coming into contact with the eyes of the wearer 6. Also, the band pad 67 provides a cushion for the forehead of the wearer 6 while the helmetless support system 2 rests on the head of the wearer 6.

Regarding FIG. 3, there is shown surgical gown 4 having surgical hood 14. As shown in FIG. 3, surgical hood 14 includes a conventional clear faceplate 12 and faceplate attachments 10. It is to be understood that surgical hood 14 and faceplate 12 are to be constructed of a one-piece design.

A further unique aspect of the present invention is the use of faceplate attachments 10. Faceplate attachments 10 can be conventionally attached to the side of faceplate 12 that will be closest to the wearer 6 and above the top of faceplate 12 by conventional fasteners, adhesives, or the like, Preferably, faceplate attachments 10 are constructed of hook and loop fasteners (Velcro®) or magnets that will allow faceplate 12 to be easily attached to and removed from front offsets 53, as will be discussed in greater detail later. It is to be understood that the number of faceplate attachments 10 should equal the number of front offsets 53. Furthermore, faceplate attachments 10 should be spaced across the side of faceplate 12 that will be closest to the wearer 6 in order to allow the faceplate 12 to be located at a predetermined distance from the face of the wearer 6.

Attaching the Surgical Hood and Gown to the Helmetless Support

In order to attach surgical gown 4 and surgical hood 14 to the helmetless support 50, attention is directed to FIGS. 1-5. The wearer 6 conventionally dons the one-piece surgical gown or toga 4 but does not place the surgical hood 14 over the head of the wearer 6. The wearer 6 then attaches the flexible band 52 around the head of the wearer 6. It is to be understood that the wearer 6 may adjust the height of the helmetless support 50 and circumference of the flexible band 52, as discussed earlier. As shown in FIG. 4, once the wearer 6 has attached the helmetless surgical hood and gown support 50 to the head of the wearer 6, the wearer 6 conventionally attaches the faceplate attachments 10 to the faceplate attachments 54 of front offsets 53 and pulls the hood 14 over the head of the wearer 6. In this manner, the surgical hood 14 is now securely attached to the helmetless surgical hood and gown support 50 and a portion of the hood 14 rests upon the adjustable headband 60 so that surgical gown 4 and surgical hood 14 are supported by helmetless surgical hood and gown support 50.

Figure 5:
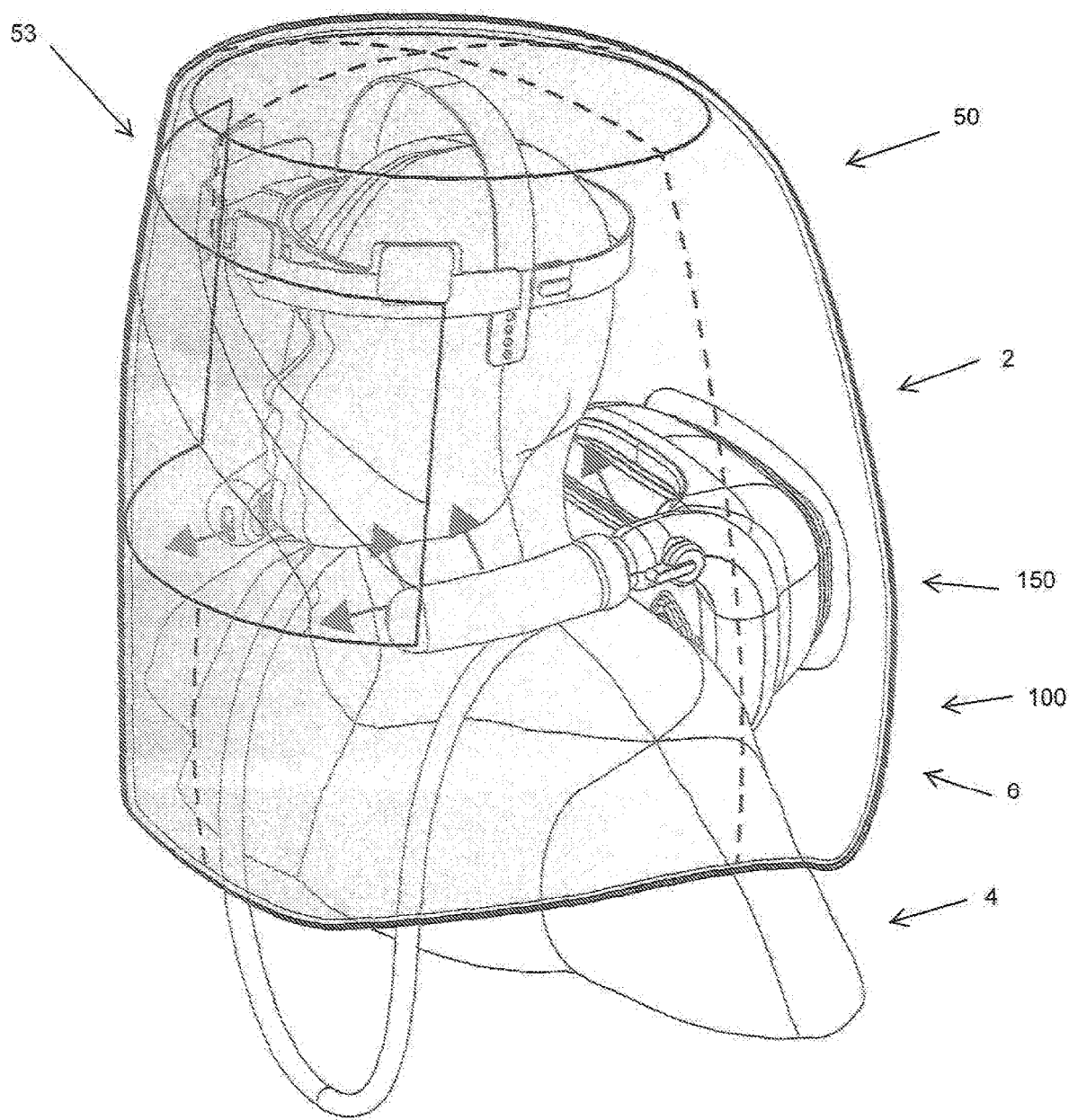
FIG. 5 is a schematic, isometric, front view of the helmetless support for use with surgical hoods and gowns with the ventilation system being installed, according to one embodiment of the present invention.
Figure 6:
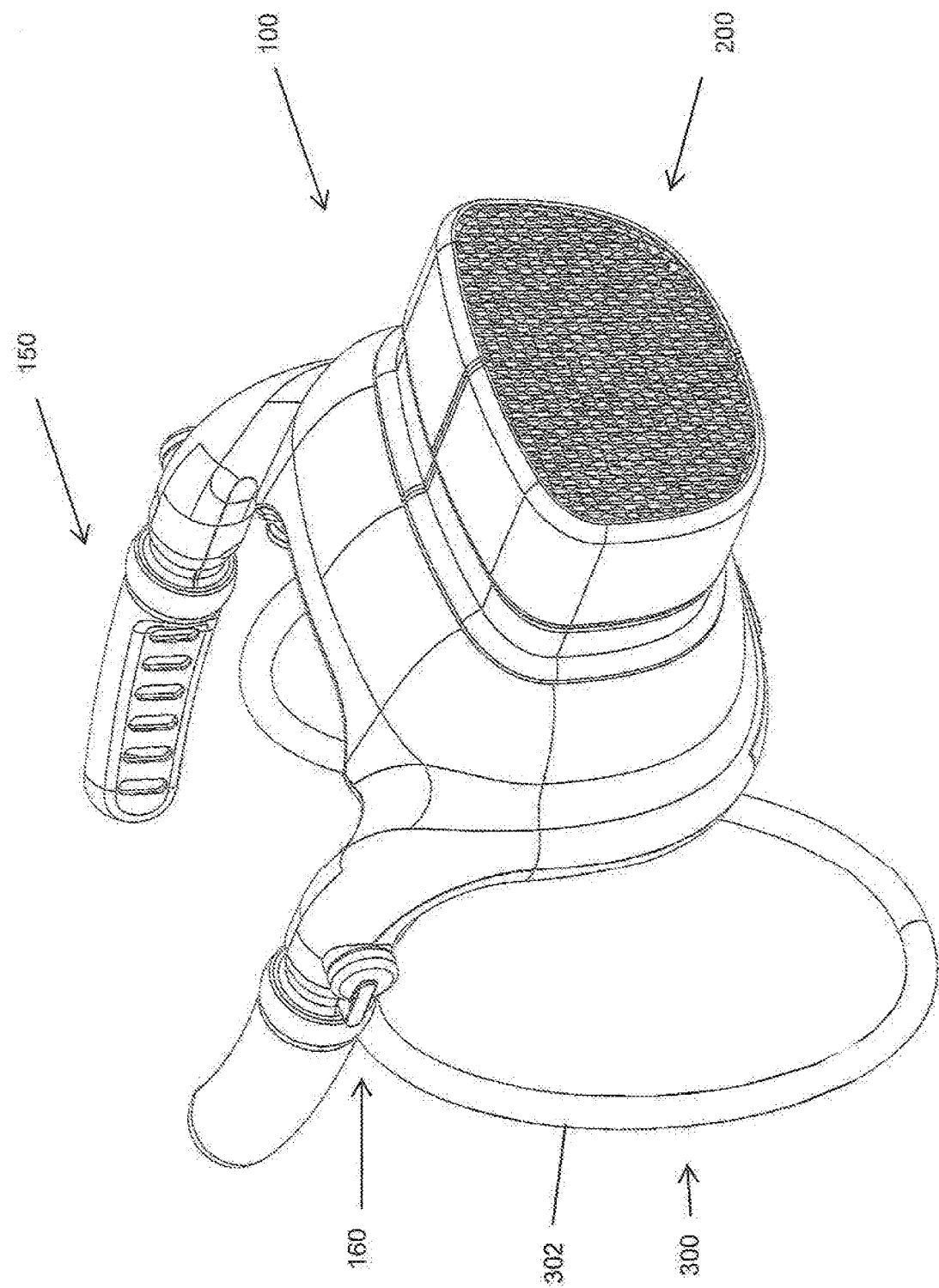
FIG. 6 is a schematic, isometric, front view of a ventilation system for use with surgical hoods and gowns, constructed according to an embodiment of the present invention.
Figure 7:
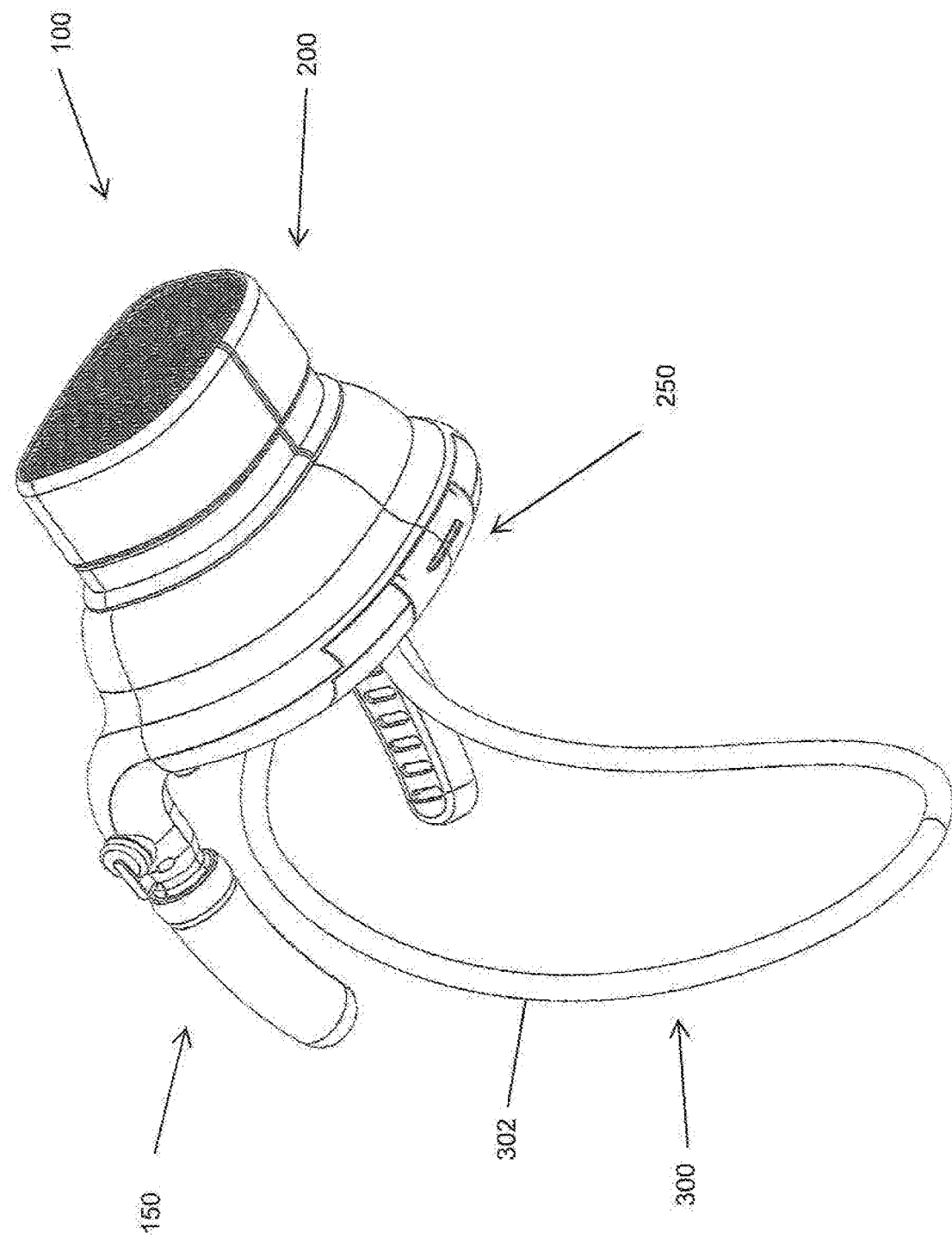
FIG. 7 is a schematic, isometric, bottom view of the ventilation system for use with surgical hoods and gowns, constructed according to an embodiment of the present invention.

As shown in FIGS. 1-5, surgical hood 14 has now been placed completely over the head of wearer 6. In this manner, the helmetless support 50 now supports the surgical hood 14 and faceplate 12 so that the wearer 6 is now completely and sterilely covered by the surgical gown 4 and surgical hood 14. Furthermore, the helmetless support 50 keeps the faceplate 12 away from the face of the wearer 6 and the hood 14 away from the top and back of the head of the wearer 6 in order to allow air to flow from the ventilation system 100 around the head of the wearer 6 (FIG. 5).

Helmetless Surgical Hood and Gown Ventilation System

Referring now to FIGS. 5-16, there is illustrated a helmetless support system 2 for use with surgical hoods and gowns including a ventilation system 100. The helmetless support system 2 for use with surgical hoods and gowns including a ventilation system 100 can be used to support the one-piece surgical gown 4 and the surgical hood 14 without the need for the wearer 6 to wear a helmet. In this manner, the one-piece surgical gown 4 and the surgical hood 14 completely and sterilely cover the wearer. Also, the one-piece surgical gown 4 and the surgical hood 14 includes a clear faceplate 12. The helmetless support system 2 for use with surgical hoods and gowns further includes ventilation system 100 such that the wearer 6 can control the fan speed once the gown 4 and hood 14 have been donned. A face vent module 150 is used as a "yoke" to support the ventilation system 100 on the shoulders of the wearer 6. Finally, the wearer 6 can control the output from each of the various output apertures (face vent module 15, neck vent module 350, and down tube module 400 in the ventilation system 100, as will be discussed in greater detail later.

As shown in FIGS. 9-12, helmetless support 2 for use with surgical hoods and gowns having ventilation system 100 includes, in part, protective casing 120, face vent module 150, air filtration module 200, power module 250, yoke module 300, neck vent module 350, down tube module 400, air flow generation module 450, and printed circuit board (PCB) module 500.

Figure 19:
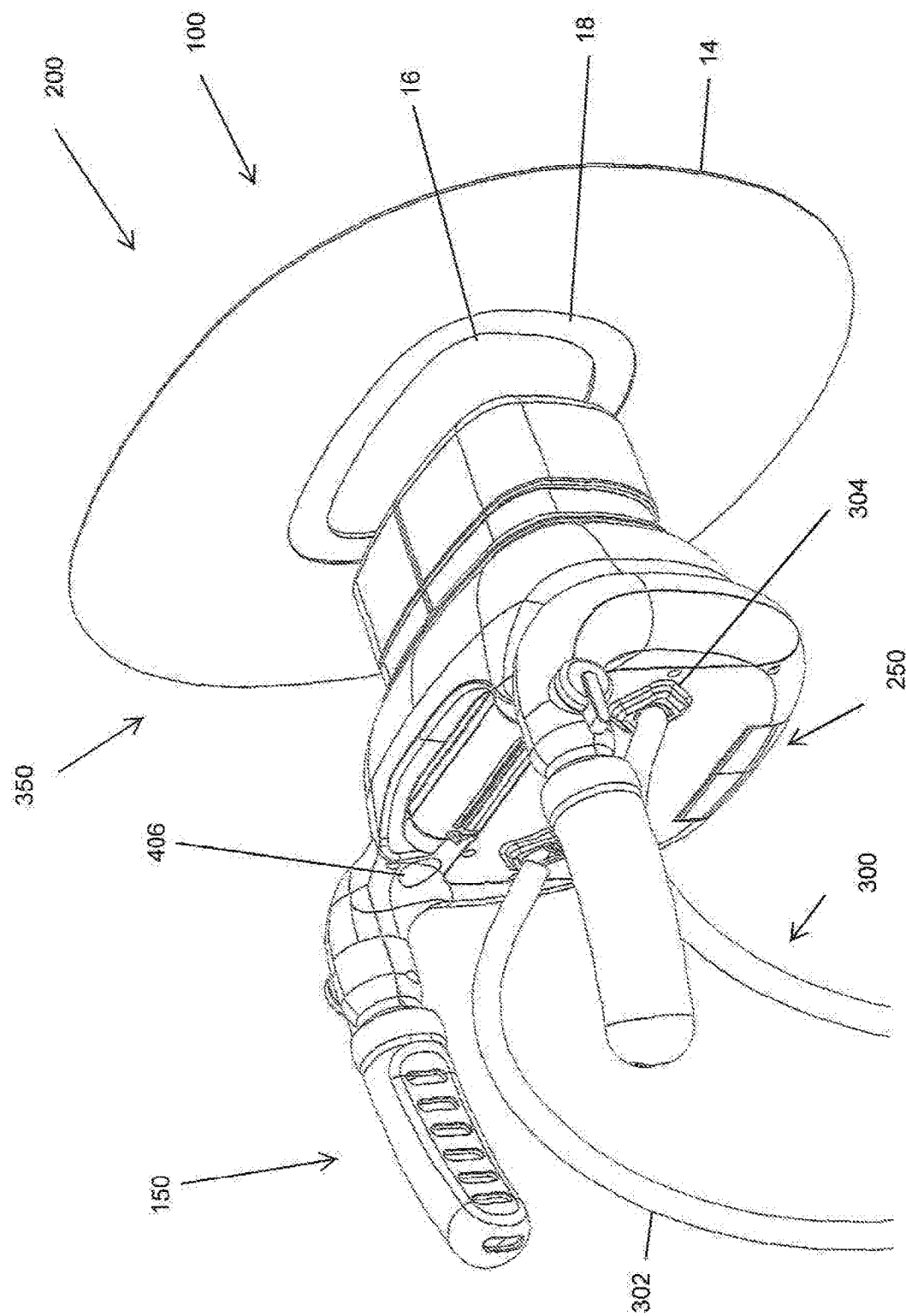
FIG. 19 is a schematic, isometric, front view of a ventilation system for use with surgical hoods and gowns showing the surgical gown being attached to the ventilation system, constructed according to an embodiment of the present invention.
Figure 20:
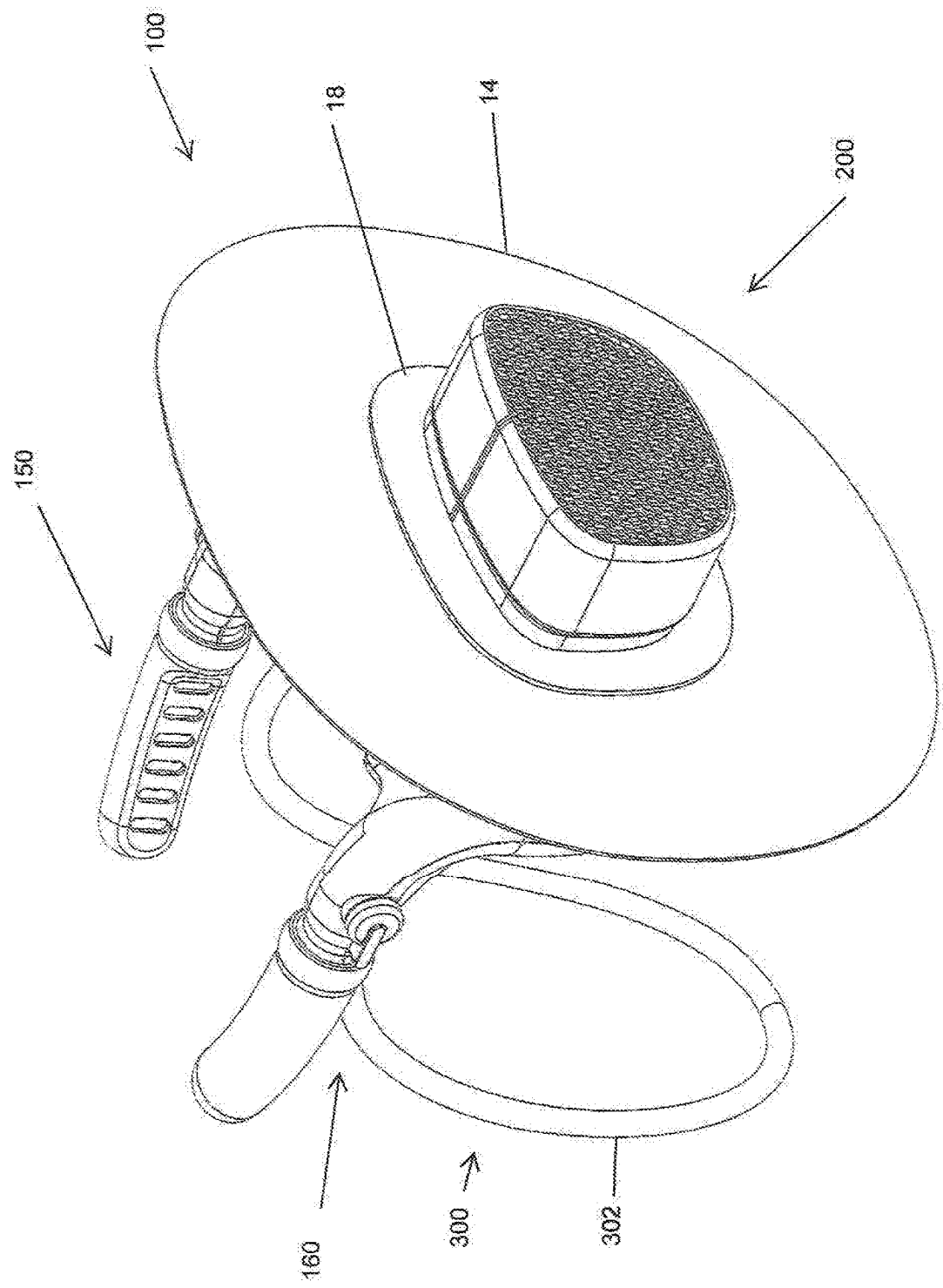
FIG. 20 is a schematic, isometric, rear view of a ventilation system for use with surgical hoods and gowns showing the surgical gown being attached to the ventilation system, constructed according to an embodiment of the present invention.

A unique aspect of the present invention is the location, of the ventilation system with respect to the surgical gown 4 and surgical hood 14. As shown in FIGS. 19 and 20, in another embodiment of the present invention, the ventilation system 100 is almost completely located inside of the surgical gown 4 and surgical hood 14. An opening 16 is conventionally constructed in the surgical hood 14 so that only a portion of the filter module 200, preferably the air filter 202, extends outside of the surgical hood 14. In particular, the opening 16 is connected to the air filtration adaptor 204. Furthermore, the area around the opening 16 and the air filtration adaptor 204 is conventionally sealed using seal 18 in order to substantially prevent any contaminants from entering into the surgical hood 14 and the surgical gown 4. Preferably, the seal 18 around the opening 16 is constructed of a thermoplastic elastomer polymeric material such as an extruded elastic polyurethane film that is flexible, exhibits high traction and sealing abilities, but with increased resistance to heat, weathering, and chemicals. In this manner, the seal 18 around the opening 16 can be used to easily remove the surgical hood 14 and surgical gown 4 from the ventilation system 100, in particular, the air filtration adaptor 204.

Figure 21:
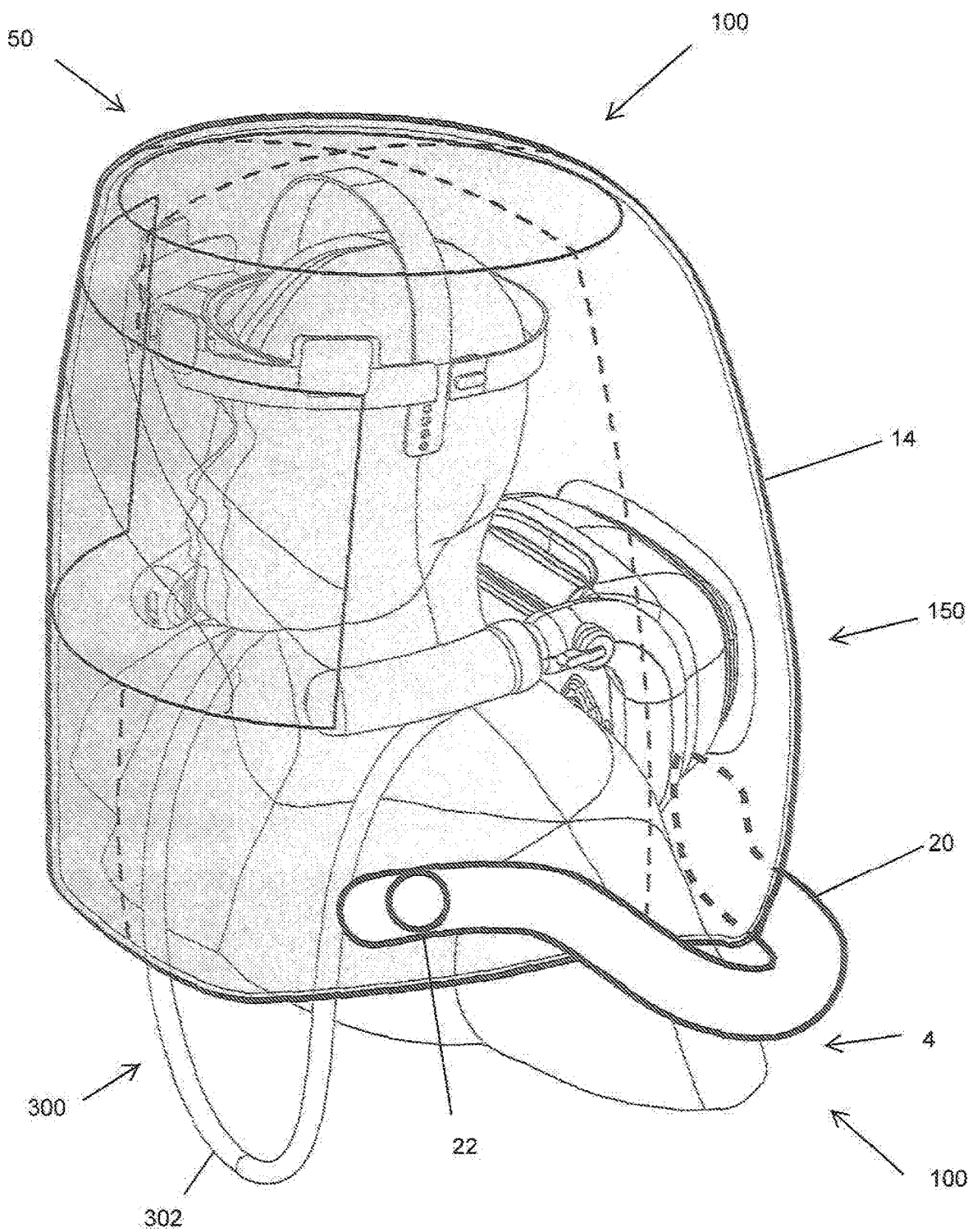
FIG. 21 is a schematic, isometric, front view, of a ventilation system for use with surgical hoods and gowns showing the lanyard being attached to the surgical hood, constructed according to an embodiment of the present invention.

In another unique aspect of the present invention, as shown in FIG. 21, in another embodiment of the present invention, it is to be understood that a lanyard 20 (FIG. 21) is located adjacent to the shoulder region of the gown 4 such that the lanyard 20 is releasably attached to the shoulder region of the gown 4, wherein the lanyard 20 may be used when self-doffing (removing) the gown 4 by the wearer 6 in order to facilitate removal of the gown 4 from the filter adaptor 204 at the interface between the opening 16 and the filter adaptor 204. In particular, the wearer 6 grabs lanyard handle 22 and pulls on lanyard 20. The pulling action on lanyard 20 will cause the gown 4 to be removed from the filter adaptor 204 at the interface between the opening 16 and the filter adaptor 204.

Protective Casing 120

With respect to protective casing 120, protective casing 120, preferably, is constructed of any suitable, durable, high strength, shock resistant, UV resistant, medical grade polymeric material. It is to be understood that protective casing 120 is used to encase ventilation system 100 in order to provide protection for air filtration module 200, power module 250, neck vent module 350, down tube module 400, air flow generation module 450, and printed circuit board (PCB) module 500.

Face Vent Module 150

Regarding face vent module 150, as shown in FIGS. 5-11, face vent module 150, includes, in part, removable face vents 152, face vent openings 154, face vent connectors 156, face vent adaptors 158, face vent air flow adjustors 160, and face vent air flow adjuster lever 162. Preferably, face vents 152 and face vent connectors 156 are constructed as a single-piece construction and are constructed of any suitable, durable, lightweight, medical grade, washable material. Also, face vent openings 154 are formed in removable face vents 152 by conventional techniques such as forming, stamping, molding, or the like. Face vent adaptors 158, preferably, are constructed of any suitable, durable, high strength, medical grade material and are permanently connected to protective casing 180 near face vent air flow adjustors 160 and face vent air flow adjuster levers 162. Finally, face vent air flow adjustors 160 and face vent air flow adjuster lever 162, preferably, are constructed of any suitable, durable, high strength, medical grade material.

A unique aspect of the present invention is the use of removable face vents 152. In particular, removable face vents 152 are constructed in such a manner that allows the removable face vents 152 to be easily removed from the face vent adaptors 158 so that the removable face vents 152 can be cleaned, disinfected, and sanitized prior to the next usage of the helmetless support 2 for use with surgical hoods and gowns having ventilation system 100. Once the removable face vents 152 have been cleaned, disinfected, and sanitized, the removable face vents 152 can be easily slid onto the face vent adaptors 158 by locating the face vent connectors 156 on the face vent adaptors 158.

Another unique aspect of the present invention is that the angle at which the removable face vents 152 direct air towards the face of the wearer 6 can be adjusted. In particular, the wearer 6 can rotate the removable face vents 152 along the direction of arrows B (FIG. 9) so that the air is directed either higher up on lower down on the face of the wearer 6.

A further unique aspect of the present invention is the use of face vent air flow adjustors 160 and face vent air flow adjuster lever 162. In particular, the wearer 6 can adjust the amount of air flow that is being emitted out of the removable face vents 152 through the use of vent air flow adjustor 160 and face vent air flow adjuster lever 162. In this manner, the wearer 6 can conventionally manipulate face vent air flow adjuster lever 162 so that the amount of air flow is adjusted. For example, the wearer 6 may push/pull the face vent air flow adjuster lever 162 upwards which will cause the amount of air flow being emitted out of the removable face vents 152 to be reduced. Conversely, the wearer 6 may push/pull the face vent air flow adjuster lever 162 downwards which will cause the amount of air flow being emitted out of the removable face vents 152 to be increased.

Air Filtration Module 200

With respect to air filtration module 200, as shown in FIGS. 5-11 and 15, air filtration module 200, includes, in part, air filter 202 and air filtration adaptor 204. Preferably, air filter 202 is a HEPA (or ULPA) air filter that is located within a filter casing 206. Preferably, filter casing 206 is constructed of any suitable, durable, high strength, medical grade material. Preferably, air filtration adaptor 204 is conventionally formed on protective casing 120.

Figure 9:
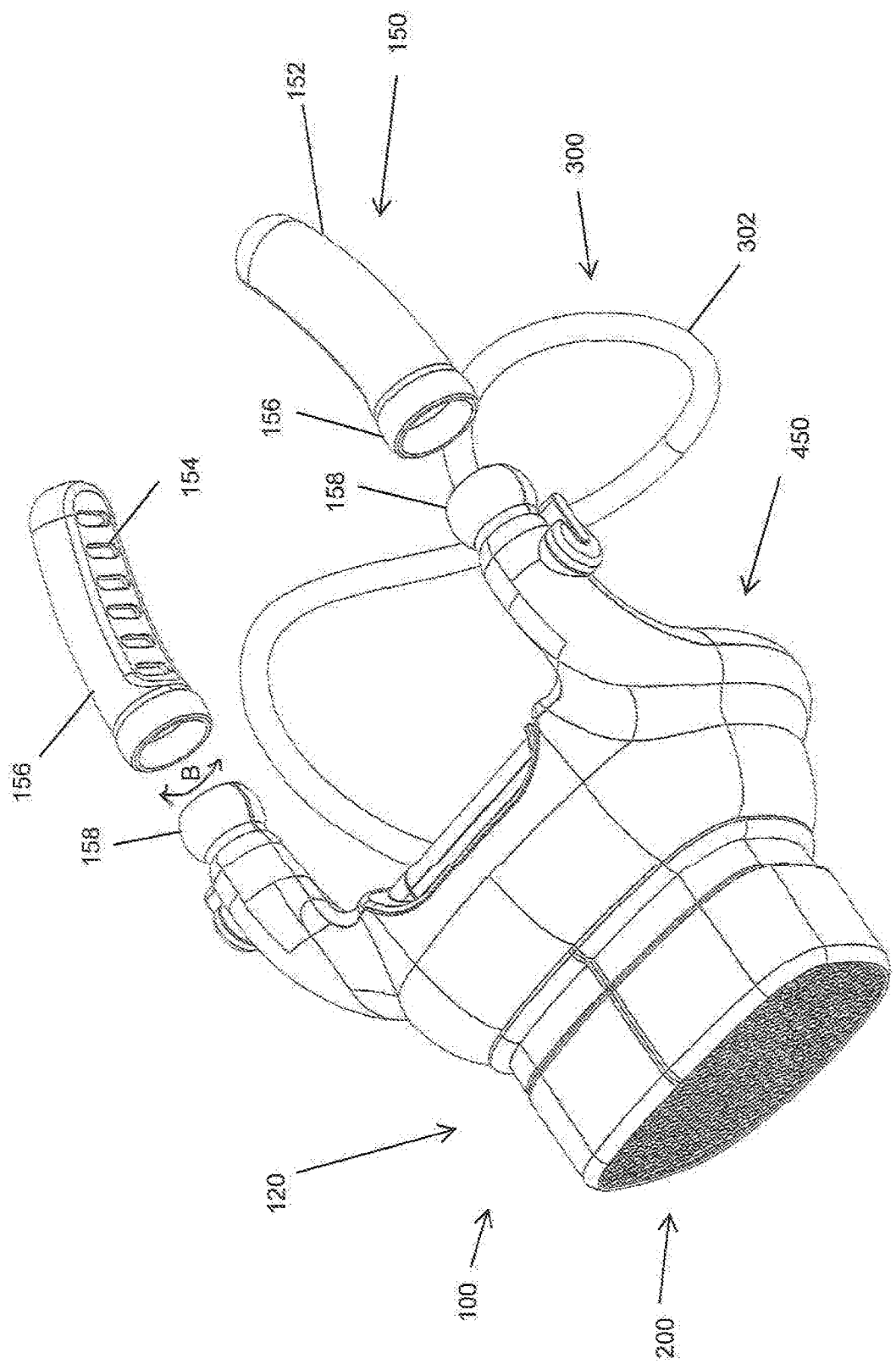
FIG. 9 is a schematic, isometric, top view of the ventilation system for use with surgical hoods and gowns with the face vents removed, constructed according to an embodiment of the present invention.
Figure 10:
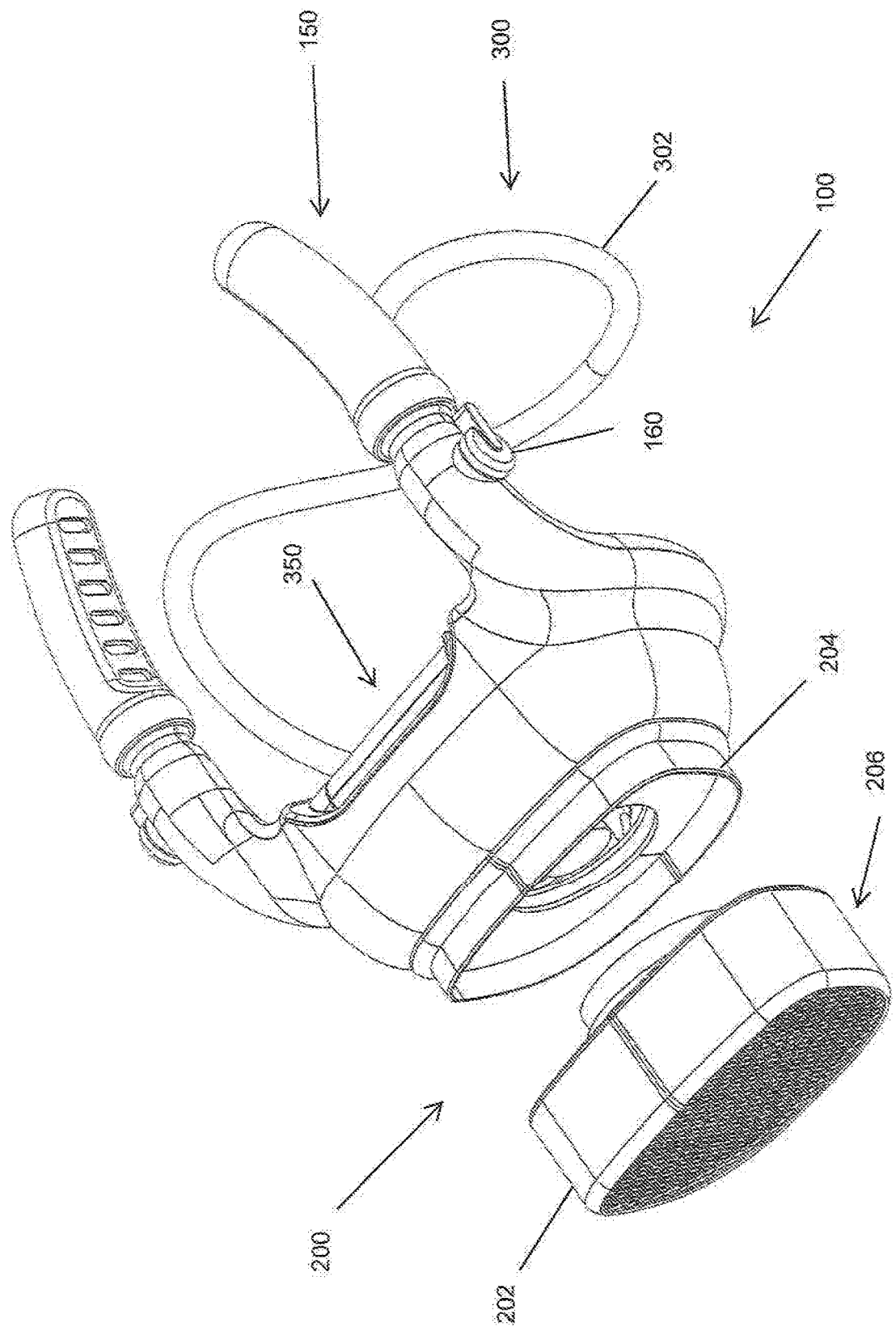
FIG. 10 is a schematic, isometric, top view of the ventilation system for use with surgical hoods and gowns with the air filter removed, constructed according to an embodiment of the present invention.
Figure 11:
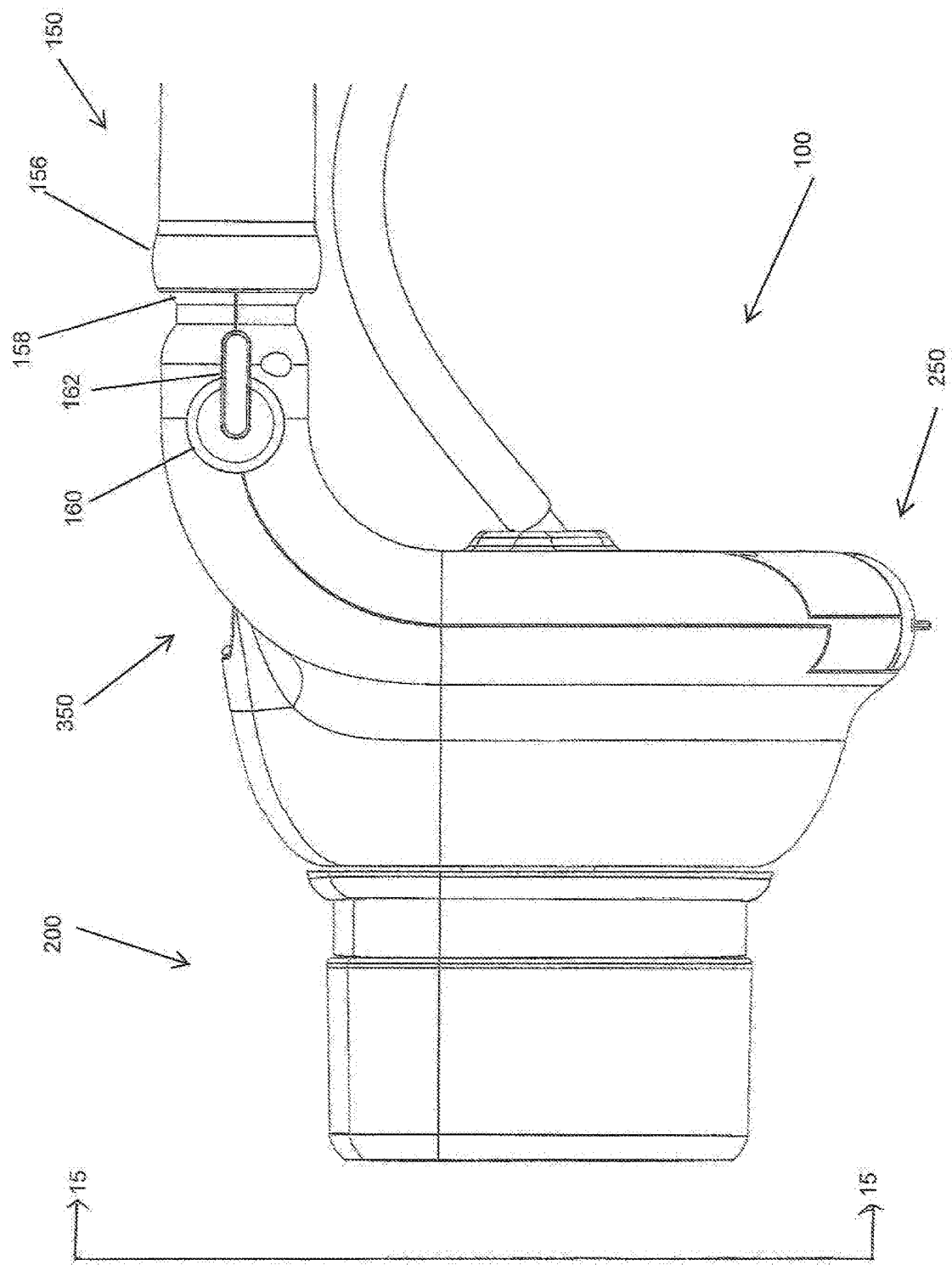
FIG. 11 is a schematic, side view of the ventilation system for use with surgical hoods and gowns illustrating the adjustable face vent air flow levers, constructed according to an embodiment of the present invention.

A unique aspect of the present invention is the use of air filtration module 200. In particular, air filtration module 200 can be used to filter out air borne contaminants so that they do enter into the surgical hood 14 and surgical gown 4. As discussed above, only the air filter 202 extends outside of the surgical hood 14 (FIG. 9). In this manner, only air going through the air filtration module 200 will be allowed to enter into the surgical hood 14 and surgical gown 4. Also, the air filter 202 can be easily removed and replaced. For example, the wearer 6 can simply remove the air filter 202 and the filter casing 206 from the air filtration adaptor 204. The wearer 6 can then replace the used air filter 202 and filter casing 206 with a new air filter 202 and filter casing 206 by simply placing the new air filter 202 and filter casing 206 onto the air filtration adaptor 204. It is to be understood that the air filter 202 and filter casing 206 can be retained on the air filtration adaptor 204 by a snap fit, a threaded connection, a bayonet connection, a slidable connection or the like.

Power Module 250

Regarding power module 250, as shown in FIGS. 7, 8, 11, 13, 15, 17, and 18, power module 250, includes, in part, battery 25, battery doors 254, and battery lock 256. Preferably, battery 252 is a conventional, rechargeable battery such as a lithium-ion battery or the like that is capable of providing sufficient power to air flow generation module 450 and printed circuit board (PCB) module 500 for an extended period of time such as 6-8 hours. Also, battery doors 254, preferably are constructed of any suitable, durable, high strength, medical grade material.

Another unique aspect of the present invention is the use of battery doors 254. Battery doors 254 are conventionally connected to protective casing 120 so that battery doors 254 can swing (or pivot) open so that battery 252 can be easily installed into power module 250 or removed from power module 250. In particular, the wearer 6 can remove battery 252 from power module 250 by opening battery doors 254 and removing battery 252 from power module 250. The battery 252 can then be placed on a conventional battery charger (not shown). Once the battery 252 has been fully charged, the wearer 6 can then remove the battery charger, open the battery doors 254, and slide the battery 252 into the power module 250 so that the battery 252 is securely retained within the power module 250. The wearer 6 then closes the battery doors 254 so that the battery 252 is not exposed to the elements. It is to be understood that a conventional locking mechanism 256 can be used to lock the battery 252 in place in the power module 250 so that the battery 252 does not inadvertently come loose while the ventilation system 100 is being operated.

Yoke Module 300

With respect to yoke module 300, as shown in FIGS. 7-10, 12 13, 17, an 18, yoke module 300, includes, in part, yoke 302 and yoke connectors 304. Preferably, yoke 302 is constructed of any suitable, durable, high strength, flexible, medical grade material. Preferably, yoke connectors 304 are attached to the back of protective casing 120.

Another unique aspect of the present invention is the use of yoke module 300. In particular, yoke module 300 can be used to assist in retaining ventilation system 100 on the shoulders of the wearer 6. In particular, yoke 302 is removably attached to protective casing through the use of yoke connectors 304. In this manner, yoke 302 can be easily attached to and removed from protective casing 120. Furthermore, since yoke 302 is flexible, yoke 302 can be adjusted so as to fit the upper torso of the wearer 6 so that ventilation system 100 will remain securely retained on the shoulders and the upper torso of the wearer 6. For example, the wearer 6 can position the ventilation system with the yoke module 300 installed over his/her head and place the yoke module 300 on the upper torso of the wearer 6. The wearer 6 can then pull/push on yoke 302 while yoke 302 is connected to yoke connectors 304 so that yoke 302 firmly contacts the upper torso of the wearer 6 in order to assist in retaining the ventilation system 100 on the shoulders and upper torso of the wearer 6.

Neck Vent Module

Regarding neck vent module 350, as shown in FIGS. 8-10, and 12-18, neck vent module 350, includes, in part, neck vent 352, neck vent opening 354, and neck vent adjustment lever 356. Preferably, neck vent 352, neck vent opening 354, and neck vent adjustment lever 356 are constructed of any suitable, durable, high strength, medical grade material. Also, neck vent opening 354 is formed in neck vent 352 by conventional techniques such as forming, cutting, molding or the like.

Figure 12:
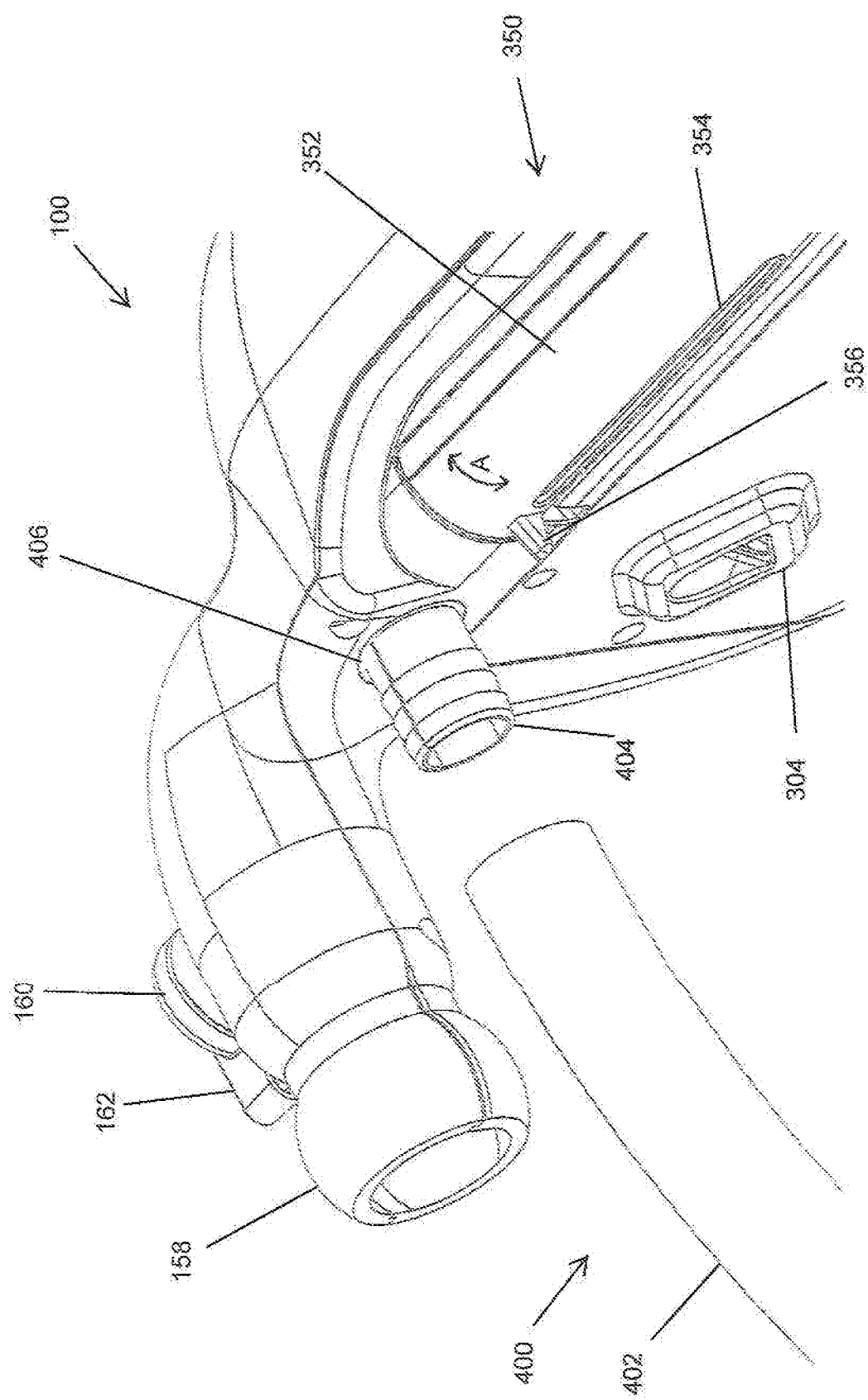
FIG. 12 is a schematic, rear view of the ventilation system for use with surgical hoods and gowns illustrating the down tube adaptors, constructed according to an embodiment of the present invention.

Another unique aspect of the present invention is the use of neck vent module 350. In particular, neck vent module 350 can be used to direct the flow of air onto the back of the neck, the upper shoulder area, and the lower back of the head of the wearer 6. For example, the wearer 6 can change the direction of the air coming out of neck vent opening 354 by manipulating the neck vent adjustment lever 356 in order to change an orientation of the neck vent 352. As shown in FIG. 12, the wearer 6 can move the neck vent adjustment lever 356 up or down along the direction of arrows A in order to direct the air coming out of neck vent opening 354 to the desired location on the back of the neck, the upper shoulder area, and the lower back of the head of the wearer 6.

Down Tube Module 400

Figure 8:
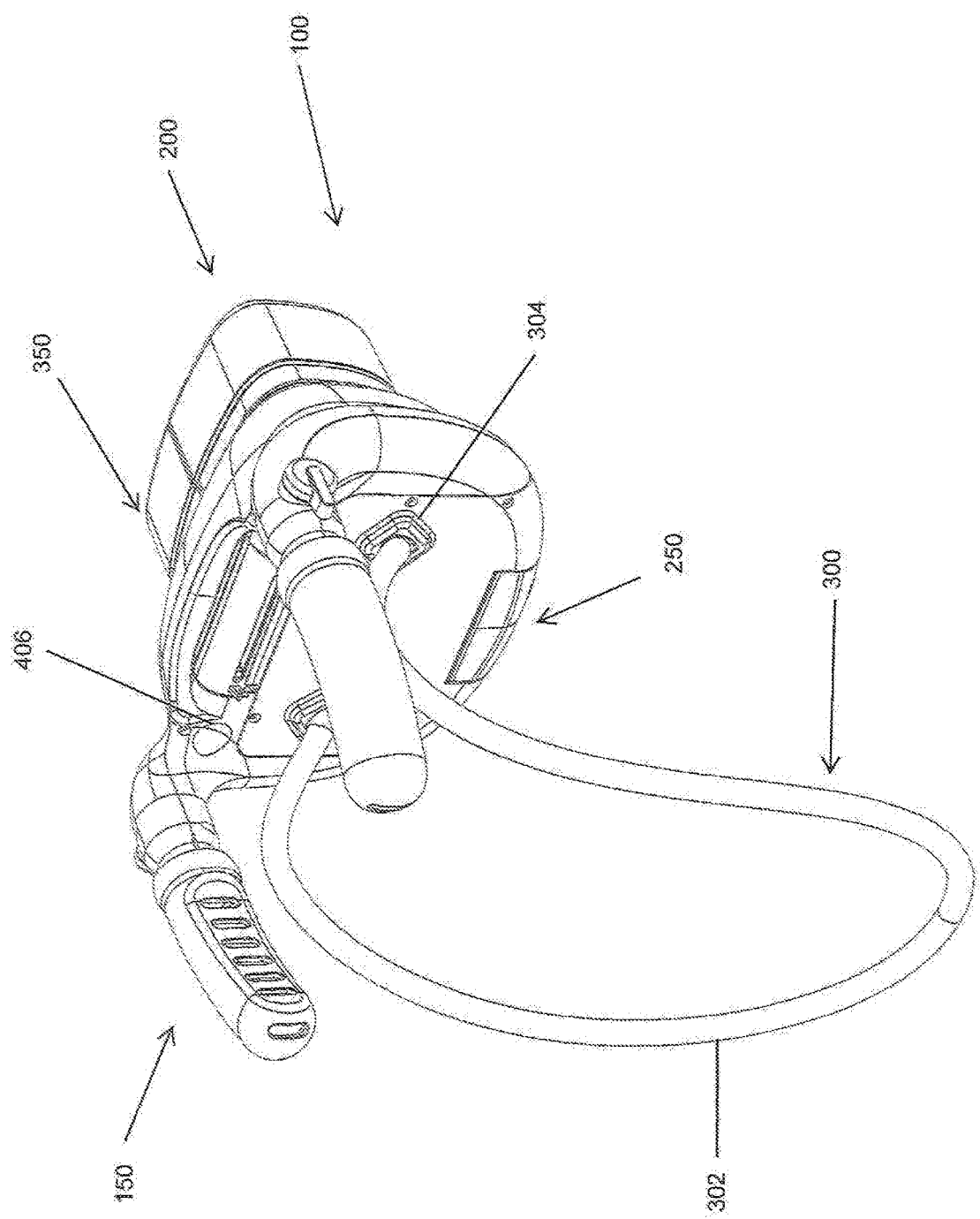
FIG. 8 is a schematic, isometric, rear view of the ventilation system for use with surgical hoods and gowns, constructed according to an embodiment of the present invention.
Figure 13:
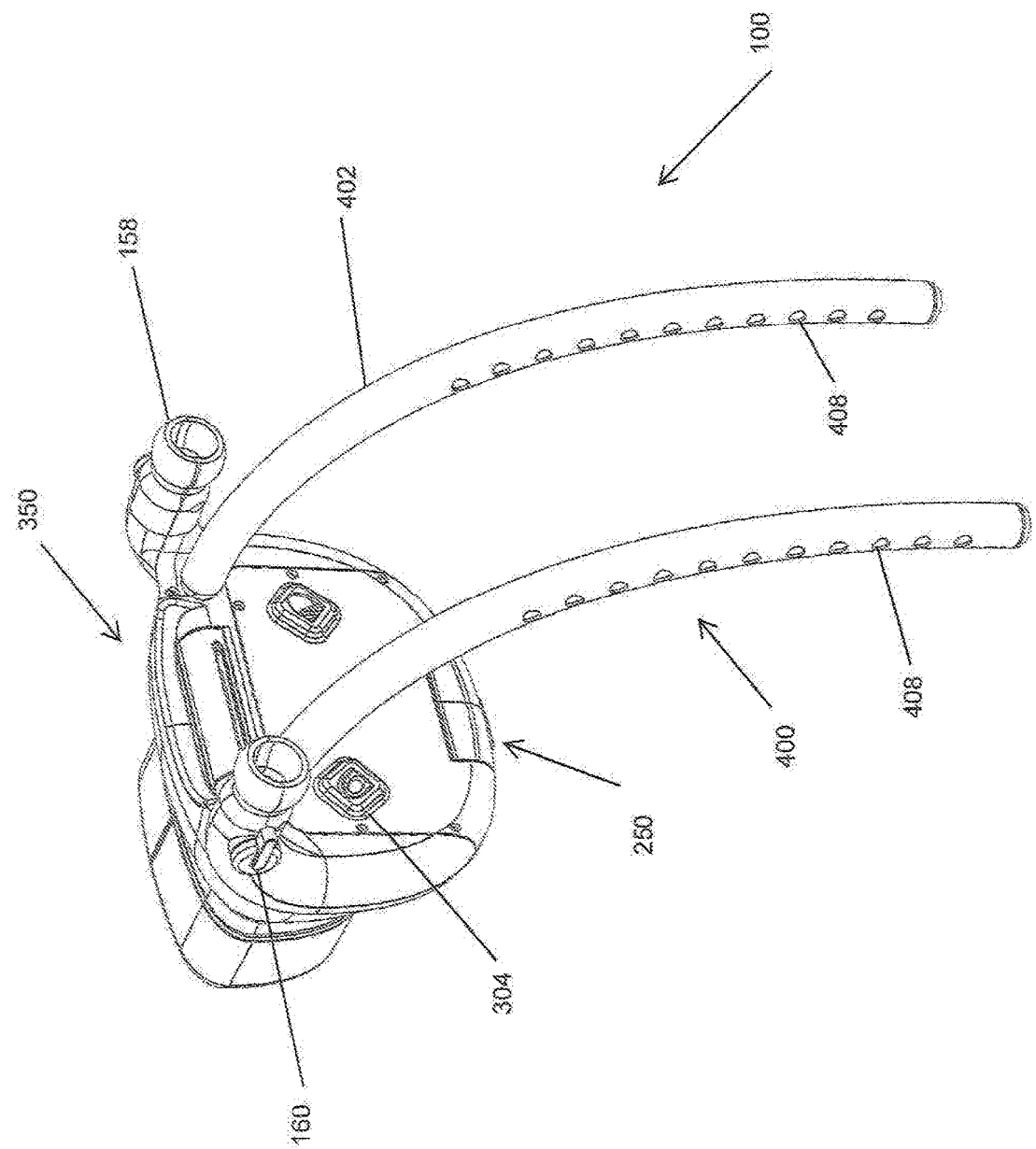
FIG. 13 is a schematic, isometric, rear view of the ventilation system for use with surgical hoods and gowns with the down tubes attached, constructed according to an embodiment of the present invention.
Figure 14:
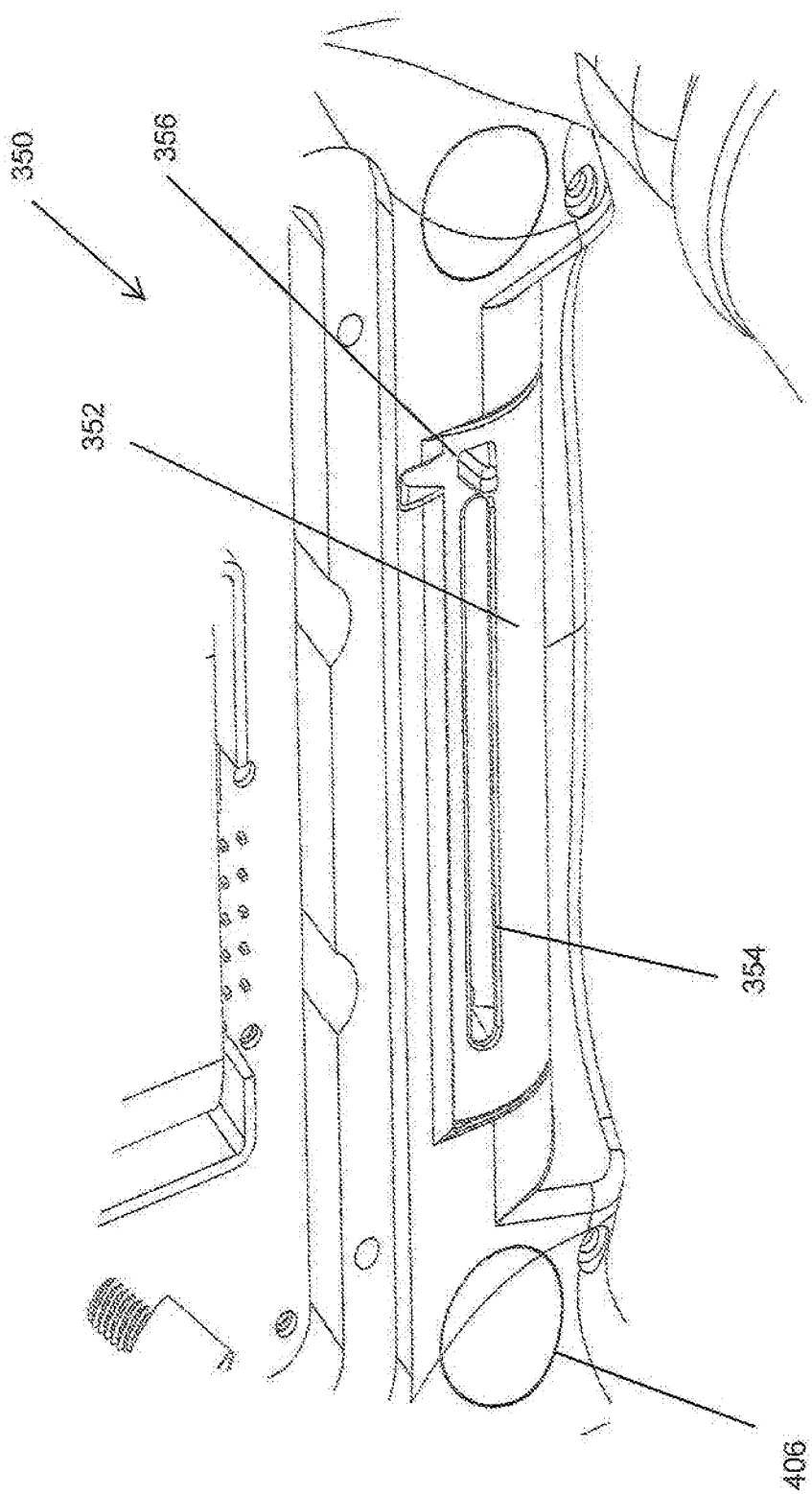
FIG. 14 is a schematic, rear view of the ventilation, system for use with surgical hoods and gowns illustrating the adjustable neck vent, constructed according to an embodiment of the present invention.

With respect to down tube module 400, as shown in FIGS. 8, 12, and 13, down tube module 400, includes, in part, down tubes 402, down tube connectors 404, down tube openings 406, and down tube air flow openings 408. Preferably, down tubes 402 are constructed of any suitable, durable, high strength, flexible, medical grade material. Also, down tube connectors 404 are constructed of any suitable, durable, high strength, rigid, medical grade material. It is to be understood that down tube air flow openings 408 are formed in down tubes 402 by conventional tube opening techniques such as forming, cutting, casting or the like. Furthermore, it is to be understood that down tubes 402 should be long enough so as to assist in providing air to the upper torso of the wearer 6, as will be described in greater detail later.

Another unique aspect of the present invention is the use of down tube module 400. In particular, down tube connectors 404 are conventionally retained within down tube openings 406. Each of the down tubes 402 are then connected at one end to a down tube connectors 404 through the use of ridges 410 on down tube connectors 404 (FIG. 12) so that the down tubes are conventionally secured to the down tube connectors 404. As the ventilation system 100 is providing air to the wearer 6, air is also being emitted from the down tube air flow openings 408 across the upper torso of the wearer 6. In this manner, the upper torso of the wearer 6 is being cooled. It is to be understood that the direction at which the air is being emitted from the down tube air flow openings 408 can be adjusted by twisted or rotating the down tubes 402.

Air Flow Generation Module 450

Figure 15:
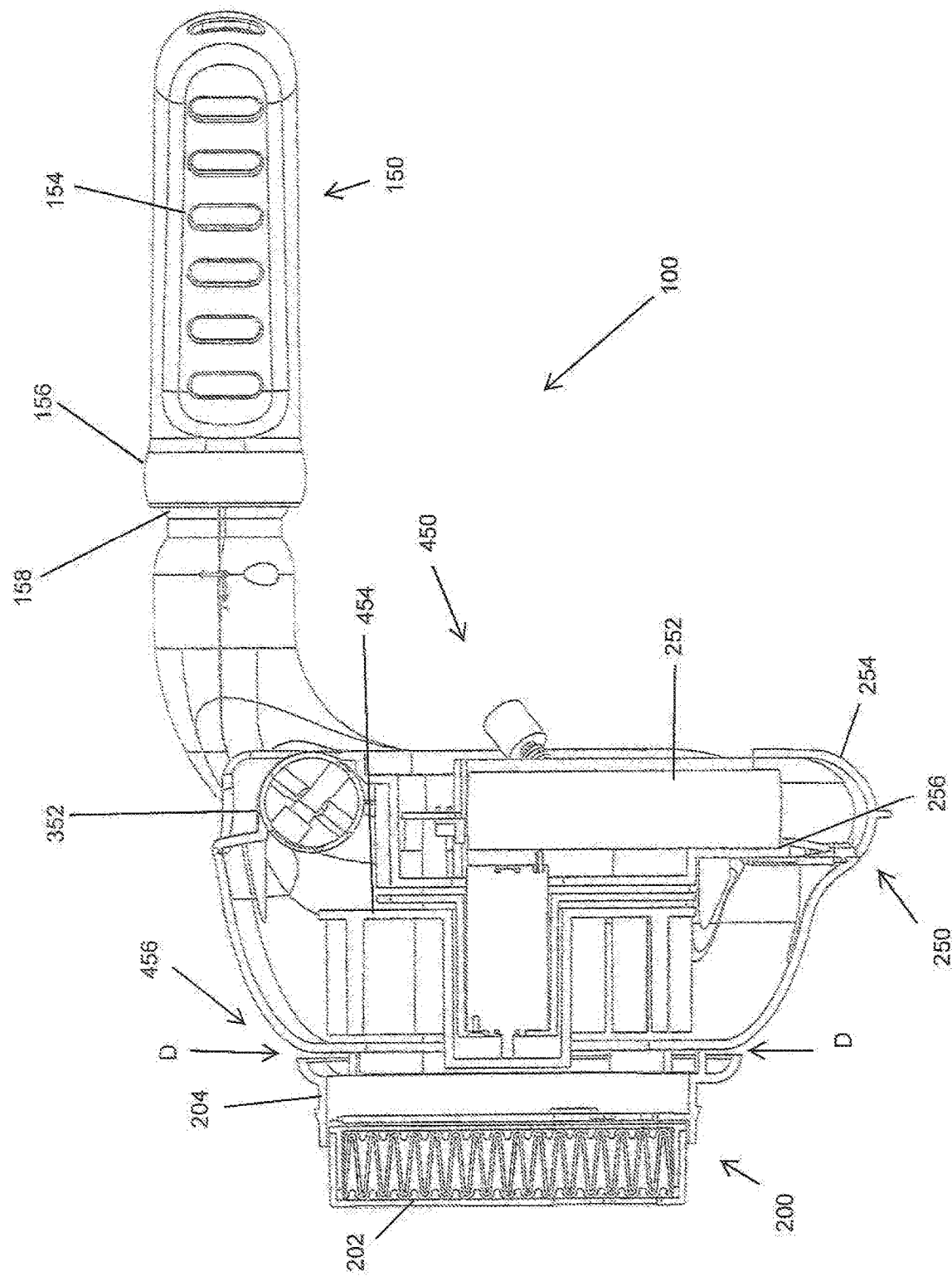
FIG. 15 is a cut-away view, taken along lines 15-15 of FIG. 11 of the ventilation system for use with surgical hoods and gowns illustrating the adjustable face vent air flow levers, constructed according to an embodiment of the present invention.
Figure 16:
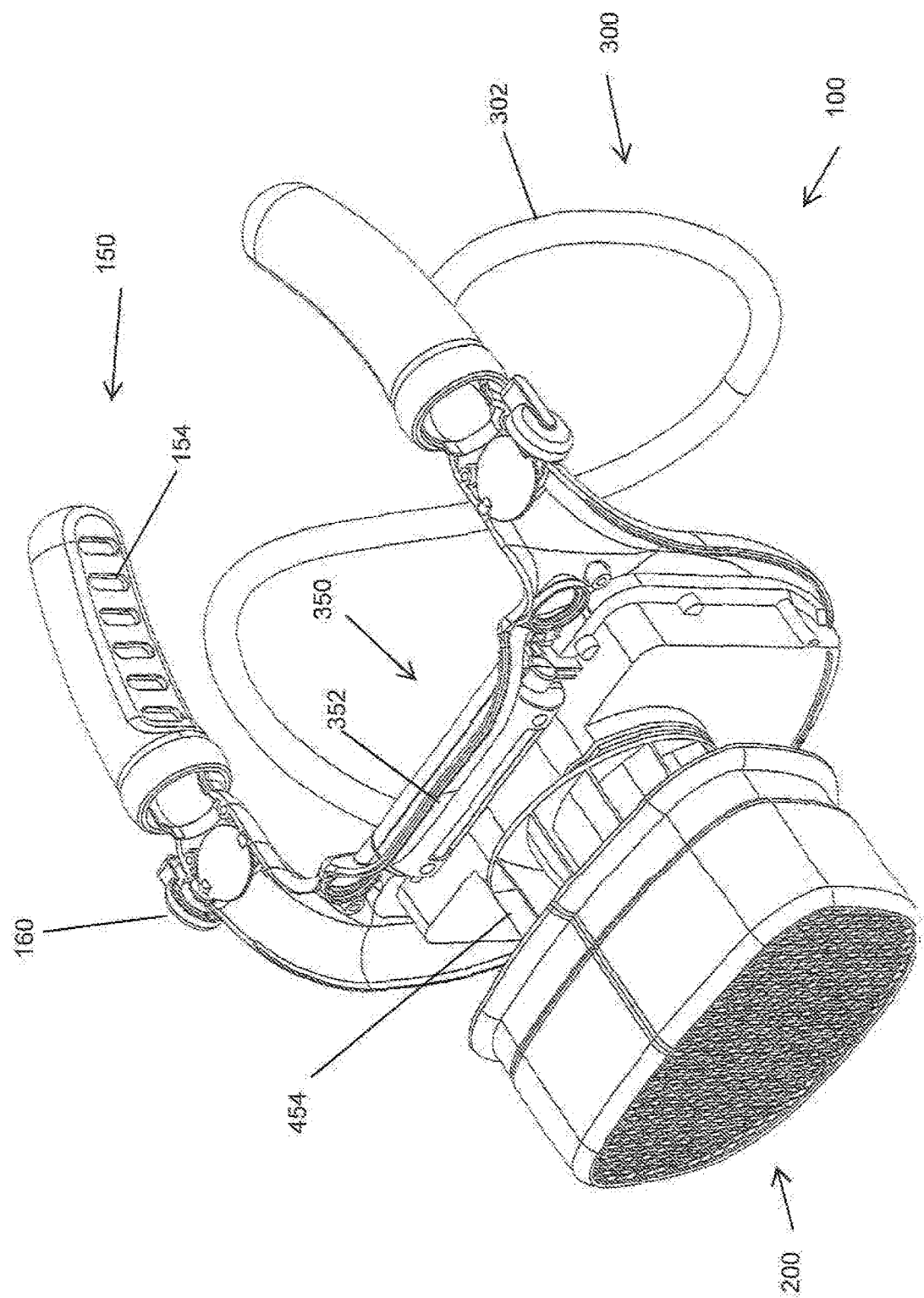
FIG. 16 is an isometric, top view of the ventilation system for use with surgical hoods and gowns with a portion of the protective casing removed, constructed according to an embodiment of the present invention.
Figure 17:
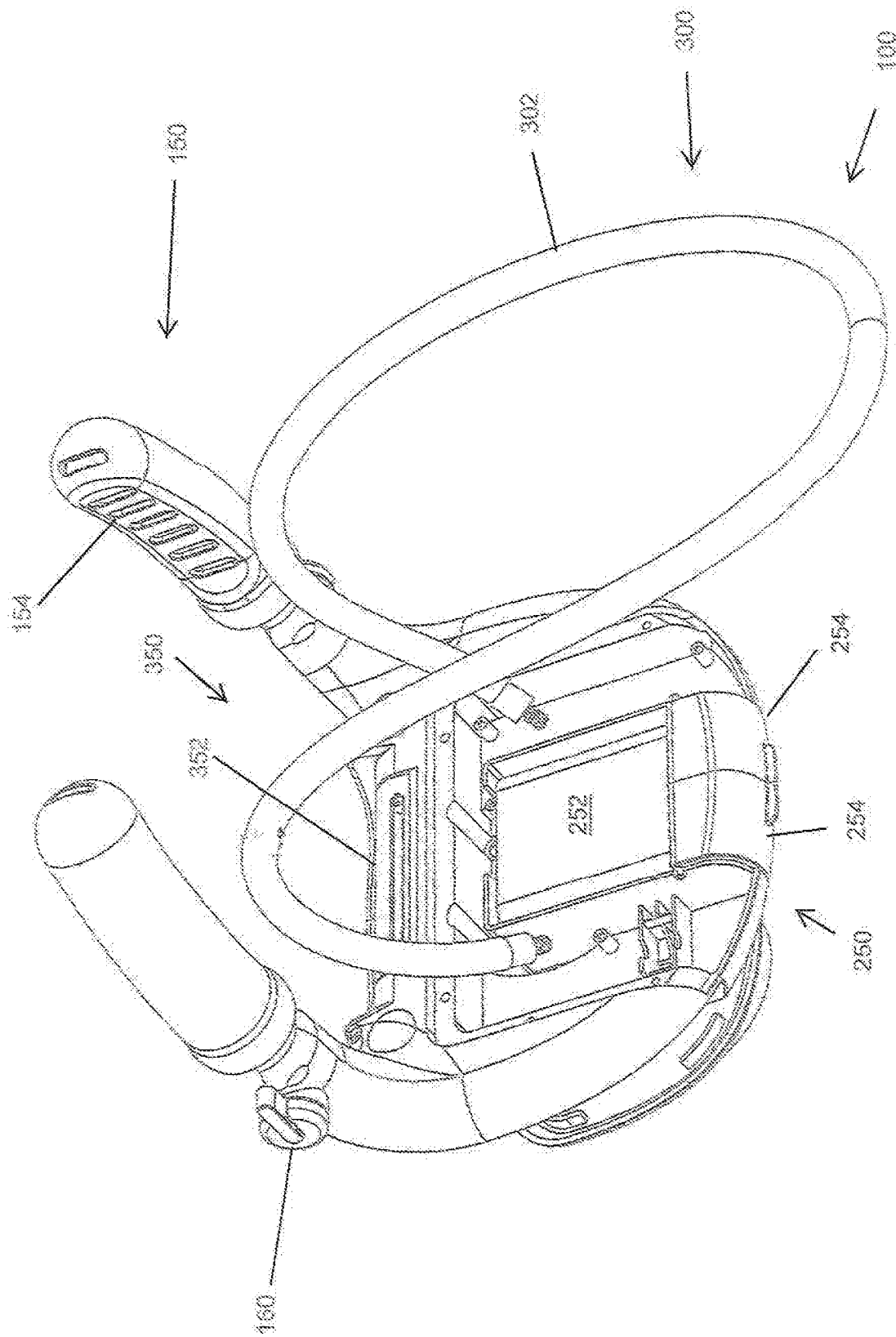
FIG. 17 is an isometric, back view of the ventilation system for use with surgical hoods and gowns with the back cover removed illustrating the power module, constructed according to an embodiment of the present invention.

Regarding air flow generation module 450, as shown in FIGS. 15 and 15, air flow generation module 450, includes, in part, conventional electrical motor 452, conventional impeller 454, and back flow opening 456. It is to be understood that battery 252 provides the electrical power to electrical motor 452.

Another unique aspect of the present invention is the use of air flow generation module 450, In particular, as the electrical motor 452 causes the impeller 454 to rotate, the configuration of the impeller 454 causes air to be drawn through the air filter module 200 in the direction of arrow C (FIG. 15). In this manner, the air filter module 200 can be used to filter the air being drawn into the ventilation system 100. Also, the back flow opening 456 is provided in order to allow air that is contained within the surgical hood 14 to also be drawn through back flow opening 456 in the direction of arrows D. In this manner, the back flow opening 456 provides for an even greater circulation of the air within the hood 14 while the ventilation system 100 is in operation. Furthermore, as shown in FIG. 15, only a portion of the filter module 200, preferably the air filter 202, extends outside of the surgical hood 14.

Printed Circuit Board (PCB) Module 500

Figure 18:
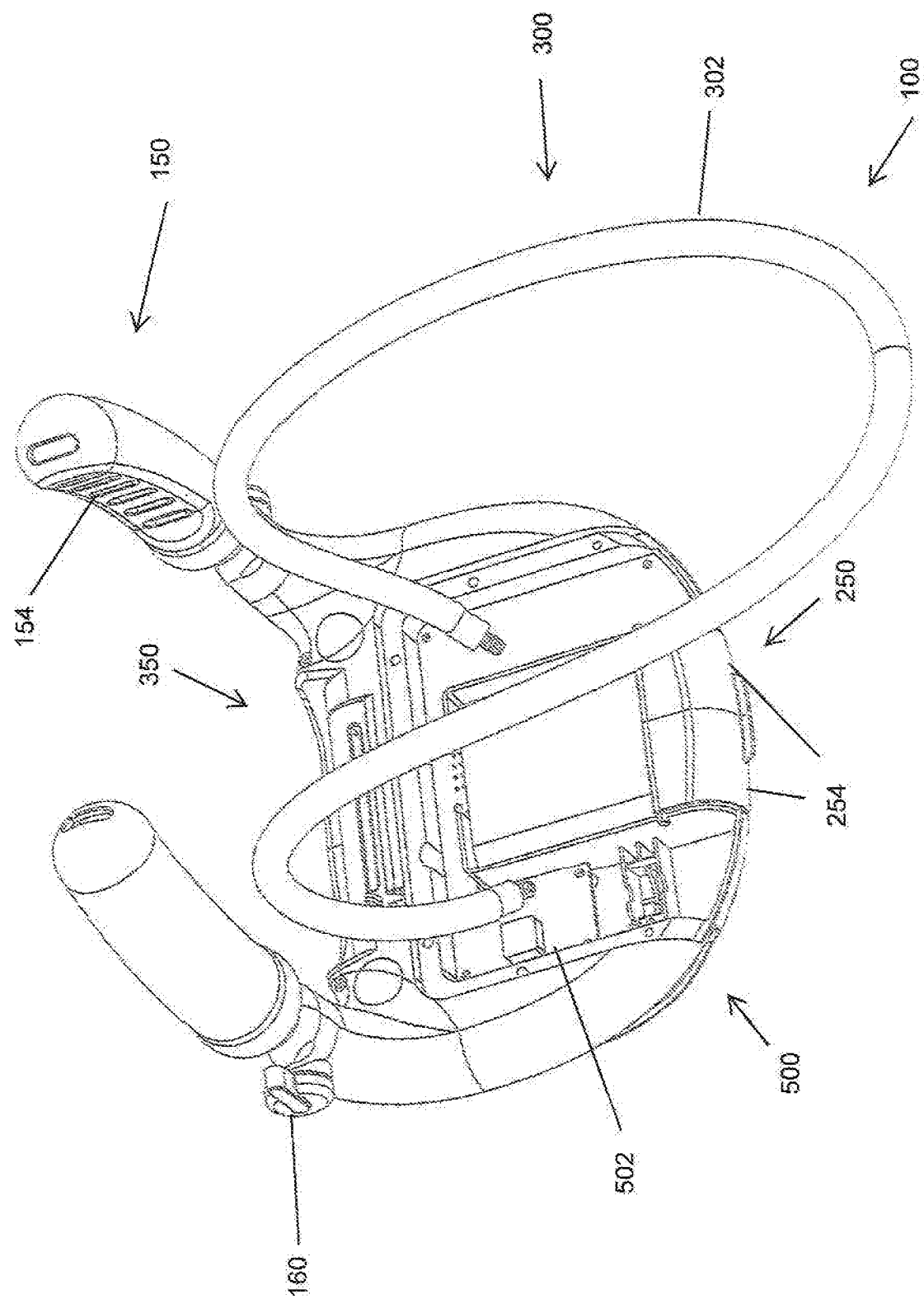
FIG. 18 is an isometric, back view of the ventilation system for use with surgical hoods and gowns with the back cover removed illustrating the printed circuit board (PCB) module, constructed according to an embodiment of the present invention.

With respect to printed circuit board (PCB) module 500, as shown in FIG. 18, printed circuit, board module 500, includes, in part, a conventional printed circuit board 502. It is to be understood that printed circuit board 502 can be used to control the ventilation system 100. In particular, printed circuit board 502 can be used to control the speed at which the impeller 454 (FIG. 15) rotates, thereby controlling the velocity of the air being emitted from the face vents 152, the neck vent 352, and the down tubes 402. It is to be further understood that the printed circuit board 502 is located in the rear of the protective casing 120 so that the printed circuit board can be located adjacent to the battery 252. Finally, it is to be understood that the printed circuit board 502 is conventionally retained within the protective casing 102 by conventional fasteners (not shown).

Operation of Helmetless Surgical Hood and Gown Ventilation System

Another unique aspect of the present invention is the use of ventilation system 100. As shown in FIGS. 5-18, as the electrical motor 452 causes the impeller 454 to rotate, the configuration of the impeller 454 causes air to be drawn through the air filter module 200 in the direction of arrow C (FIG. 15). In this manner, the air filter module 200 can be used to filter the air being drawn into the ventilation system 100. Also, the back flow opening 456 is provided in order to allow air that is contained within the hood 14 to also be drawn through back flow opening 456 in the direction of arrow D. In this manner, air (or other similar gases) is introduced into the inside of hood 14. The face vent module 150 is used as a "yoke" to support the ventilation system 100 upon the shoulders of wearer 6. As air is introduced into the inside of hood 14, face vents 152, neck vent 352, and down tubes 402 cause the air to go up and around the head of wearer 6 and across the torso of the wearer 6 in order to cool the head, neck, and torso areas of wearer 6 (FIG. 5).

The preceding merely illustrate the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising," "including," "containing," etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. Therefore, the patent may not be interpreted to be limited to the specific examples or embodiments or methods specifically and/or expressly disclosed herein Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein is a new and improved helmetless support and lightweight ventilation system for use with surgical hoods and gowns. The preferred helmetless support and lightweight ventilation system for use with surgical hoods and gowns, according to various embodiments of the present invention, offers the following advantages: ease of use; lightness in weight; durability; the ability to distribute the device weight along the shoulders of the wearer while maintaining full mobility and greatly reducing head and neck fatigue; adjustability of the fan speed: the ability to control the amount and direction of the output from each of the various ventilation system output apertures; the ability to provide a contiguous head/hood covering; the ability to filter the air contacting the wearer; the use of front offsets to provide for air circulation around the head and neck areas of the wearer; the ability to remove the face vents for ease of cleaning or sanitizing; the ability to provide air flow within the hood; and compactness of the device.

In fact, in many of the preferred embodiments, these advantages of ease of use, lightness in weight, durability, the ability to distribute the device weight along the shoulders of the wearer while maintaining full mobility and greatly reducing head and neck fatigue, adjustability of the fan speed, the ability to control the amount and direction of the output from each of the various ventilation system output apertures, the ability to provide a contiguous head/hood covering, the ability to filter the air contacting the wearer, the use of front offsets to provide for air circulation around the head and neck areas of the wearer, the ability to remove the face vents for ease of cleaning or sanitizing, the ability to provide air flow within the hood, and compactness of the device are optimized to an extent that is considerably higher than heretofore achieved in prior, known support and ventilation systems for use with surgical hoods and gowns.

What is claimed is:

1. A helmetless support and ventilation system for use with surgical hoods and gowns, comprising: a flexible band; a plurality of front offsets, wherein each of the plurality of front offsets has a first end and a second end such that the first end of each of the front offsets is operatively connected to a portion of the flexible band; an offset extension having a first end and a second end such that the second end of each of the plurality of front offsets is operatively connected to the first end of the offset extension and the offset extension is located at a predetermined distance away from the flexible band; a plurality of faceplate attachment extensions, wherein each of the plurality of faceplate attachment extensions is operatively connected to the offset extension; a plurality of support faceplate attachments, such that each of the plurality of support faceplate attachments are operatively connected on one side to each of the plurality of faceplate attachment extensions; and a ventilation system located within a surgical gown and a surgical hood for providing ventilation air within the surgical gown and the surgical hood, wherein the ventilation system is retained by shoulders of a wearer of the ventilation system in order to provide ventilation aft to a face, neck, and torso of the wearer, during use; and wherein the ventilation system is further comprised of: a protective casing; a face vent module located on one side of the protective casing; an air filtration module located on the other side of the protective casing; a power module located adjacent to the face vent module; a yoke module located between the face vent module and the power module; a neck vent module located adjacent to the yoke module; a down tube module located adjacent to the neck vent module; and an air flow generation module located between the power module and the air filtration module.

2. The helmetless support and ventilation system for use with surgical hoods and gowns, according to claim 1, wherein each of the plurality of support faceplate attachments is further comprised of:
a hook and loop fastener or a magnet.

3. The helmetless support and ventilation system for use with surgical hoods and gowns, according to claim 2, wherein the helmetless support is further comprised of:
a surgical gown having a surgical hood operatively connected to the surgical gown, wherein surgical hood includes a plurality of faceplate attachments such that the faceplate attachments are capable of being removably attached to the plurality of support faceplate attachments such that the helmetless support is used to support the surgical hood and gown.

4. The helmetless support and ventilation system for use with surgical hoods and gowns, according to claim 1, wherein the face vent module is further comprised of: a plurality of race vent connectors operatively connected to the other side of the protective casing; a plurality of removable face vents, wherein each of the plurality of removable face vents is operatively connected to each of the plurality of face vent connectors such that a position of each of the removable face vents can be adjusted; a plurality of face vent openings located substantially along a portion of each of the plurality of removable face vents; and a plurality of face vent aft flow adjustors, wherein each of the plurality of face vent flow adjustors is located adjacent to the plurality of face vent connectors.

5. The helmetless support and ventilation system for use with surgical hoods and gowns, according to claim 1, wherein the air filtration module is further comprised of; an air filtration adaptor operatively connected to the one side of the protective casing; an air filter operatively connected to the air filtration adaptor; a stretchable opening boated in a back portion of the hood that seals around the air filtration adaptor in order to ensure that all aft brought into the surgical gown and surgical hood is forced to pass through the filter; and a lanyard located adjacent to the opening and releasably connected to a portion of the surgical gown, wherein the lanyard can be used when self-doffing of the surgical gown in order to facilitate removal of the surgical hood from the air filter adaptor.

6. The helmetless support and ventilation system for use with surgical hoods and gowns, according to claim 1, wherein the yoke module is further comprised of: a plurality of yoke connectors operatively connected to the other side of the protective casing; and a yoke such that the yoke is removable connected to the plurality of yoke connectors.

7. The helmetless support and ventilation system for use with surgical hoods and gowns, according to claim 1, wherein the neck vent module is further comprised of; a neck vent operatively connected to the other side of the protective casing; a neck vent opening located along a portion of the neck vent; and a neck vent adjustment lever operatively connected to the neck vent in order to adjust an orientation of the neck vent.

8. The helmetless support and ventilation system for use with surgical hoods and gowns, according to claim 1, wherein the down tube module is further comprised of: a plurality of down tube connectors operatively connected to the other side of the protective casing; a plurality of down tubes, wherein each of the plurality of down tubes is removably connected to each of the plurality of down tube connectors; and a plurality of down tube air flow openings located along a portion of each of the plurality of down tubes.

\* \* \* \* \*